United States Patent
Li et al.

(10) Patent No.: US 10,577,665 B2
(45) Date of Patent: Mar. 3, 2020

(54) APTAMERS FOR CLOSTRIDIUM DIFFICILE DETECTION

(71) Applicant: McMaster University, Hamilton (CA)

(72) Inventors: Yingfu Li, Dundas (CA); John D. Brennan, Dundas (CA); Meng Liu, Dundas (CA)

(73) Assignee: McMaster University, Hamilton, Ontario (CA)

( * ) Notice: Subject to any disclaimer, the term of this patent is extended or adjusted under 35 U.S.C. 154(b) by 0 days.

(21) Appl. No.: 16/121,120

(22) Filed: Sep. 4, 2018

(65) Prior Publication Data

US 2019/0071714 A1 Mar. 7, 2019

Related U.S. Application Data

(60) Provisional application No. 62/554,237, filed on Sep. 5, 2017.

(51) Int. Cl.
| | | |
|---|---|---|
| C12N 15/11 | (2006.01) |
| C12Q 1/689 | (2018.01) |
| C12N 15/10 | (2006.01) |
| C12N 15/115 | (2010.01) |

(52) U.S. Cl.
CPC ......... C12Q 1/689 (2013.01); C12N 15/1048 (2013.01); C12N 15/115 (2013.01)

(58) Field of Classification Search
None
See application file for complete search history.

(56) References Cited

U.S. PATENT DOCUMENTS

| | | |
|---|---|---|
| 7,745,607 B2 | 6/2010 | Li et al. |
| 2005/0089864 A1 | 4/2005 | Li et al. |
| 2016/0289733 A1 | 10/2016 | Li et al. |

OTHER PUBLICATIONS

Liu M., Yin Q., Brennan J.D. & Li Y. Selection and characterization of DNA aptamers for detection of glutamate dehydrogenase from Clostridium difficile. Biochimie 2018, 145: 151-157.

Allali-Hassani A., Pereira M.P., Navani N.K., Brown, E. D. & Li, Y. Isolation of DNA aptamers for CDP-ribitol synthase, and characterization of their inhibitory and structural properties. ChemBioChem 2007, 8: 2052-2057.

Nutiu R. & Li Y. Structure-Switching Signaling Aptamers. J. Am. Chem. Soc. 2003, 125: 4771-4778.

Lu C.H., Yang H.H., Zhu C.L., Chen X. & Chen G.N. A Graphene Platform for Sensing Biomolecules. Angew. Chem. Int. Ed. 2009, 121: 4879-4881.

Wang Y., Li Z.H., Hu D.H., Lin C.T., Li J.H., Lin Y.H. Aptamer/Graphene oxide nanocomplex for in situ molecular probing in living cells. J. Am. Chem. Soc. 2010, 132: 9274-9276.

Liu M., Song J., Shuang S., Dong C., Brennan J.D. & Li Y. A graphene-based biosensing platform based on the release of DNA probes and rolling circle amplification. ACS Nano 2014, 8: 5564-5573.

*Primary Examiner* — Ekaterina Poliakova-Georgantas

(74) *Attorney, Agent, or Firm* — Bereskin & Parr LLP; Melanie Szweras

(57) ABSTRACT

Provided herein are aptamers, aptamer probes and biosensor systems that detect *C. difficile* glutamate dehydrogenase (GDH). Also provided are methods of detecting *C. difficile* GDH using the aptamers, probes and biosensors and methods of determining whether a subject has a *C. difficile* infection.

20 Claims, 10 Drawing Sheets

Specification includes a Sequence Listing.

APTAMERS FOR CLOSTRIDIUM DIFFICILE DETECTION

CROSS REFERENCE TO RELATED APPLICATIONS

The present application claims priority from U.S. provisional application No. 62/554,237 filed on Sep. 5, 2017, which is hereby incorporated by reference in its entirety.

INCORPORATION OF SEQUENCE LISTING

A computer readable form of the Sequence Listing "3244-P54034US01_SequenceListing.txt" (57,344 bytes), submitted via EFS-WEB and created on Sep. 4, 2018, is herein incorporated by reference.

FIELD

The present application relates to the field of nucleic acid aptamers, and in particular, to aptamers capable of binding glutamate dehydrogenase produced by *Clostridium difficile*, and methods of making and using such aptamers.

BACKGROUND

In recent years, outbreaks of healthcare-associated infections resulting from toxin-producing *Clostridium difficile* (*C. difficile*) have been widespread and are associated with increased morbidity and mortality. *C. difficile* is responsible for 90-100% of cases of pseudomembranous colitis, 15-25% of antibiotic-associated diarrheas and 60-75% of antibiotic-associated colitis.[1-4] According to a recent Canadian study, the incidence of *C. difficile* infection (CDI) in Canada is 65 CDI cases per 100,000 patient-days for adult patients admitted to hospitals, accompanied with a mortality rate of 5.7%.[5] In the United States, about 15,000-20,000 patients die annually from CDI.[6] Furthermore, the economic burden for taking care of CDI patients is significant: a hospital-acquired CDI increases the cost of otherwise matched hospitalizations by 4-fold, translating to over $1 billion in added cost annually.[7] A key to reducing the negative outcomes of CDI is rapid and accurate diagnosis so that the treatment of patients can be quickly implemented and the nosocomial spread of these infections effectively controlled.

Traditionally, CDI can be diagnosed using the cell cytotoxicity neutralization assay, which detects the presence of toxin, and is often considered to be the clinical gold standard for the detection of *C. difficile* from fecal samples.[8] This method performs with superior sensitivity but is labor-intensive, time consuming (up to 4 days) and requires skilled technicians.[9,10] Since the pathogenicity of *C. difficile* is linked to the two large toxins, toxin A (TcdA) and toxin B (TcdB), toxin enzyme immunoassays (EIAs) have proven to be a significant advancement. These assays are technically simple, fast and frequently used as standalone assays, but have low sensitivity,[11] which results in poor positive predictive values if the prevalence of TcdA/B in stool samples is relatively low (<10%).[12] Alternatively, the direct detection of genes encoding toxin A and/or toxin B has become a diagnostic target using polymerase chain reaction (PCR) technology. The main advantages of these molecular assays are high sensitivity and relatively short turnaround time.[13] However, several drawbacks, including intensive sample preparation, cost and potential for error limit their clinical utility.[14]

Recently, significant effort has been focused on the detection of a so-called common antigen for CDI, the glutamate dehydrogenase (GDH) enzyme, which is highly conserved and commonly produced by most isolates of *C. difficile* in large amounts.[15,16] Although GDH assays cannot discriminate between toxigenic and nontoxigenic strains, these assays have been proposed as initial screening tools for *C. difficile* in stool samples due to their high negative predictive values (>99%).[14,17,18] To improve the accuracy and efficiency of CDI diagnosis, two-step or three-step testing algorithms have been utilized involving a preliminary screening via GDH assay followed by a confirmatory test for positive samples using the cell cytotoxin assay, EIAs or PCR for TcdA/B.[14,19,20] For example, the Society for Healthcare Epidemiology of America (SHEA) and the Infectious Diseases Society of America (IDSA) guidelines recommend such a two-step algorithm using EIAs for GDH as an initial screening and then the cell cytotoxicity assay or toxigenic culture as the confirmatory test for GDH-positive stool samples.[21]

To date, the most commonly used tests for GDH are EIAs, which can provide rapid results, but demonstrate suboptimal clinical sensitivity, ranging from 79.2% to 98%, which varies significantly with the prevalence of CDI.[15,22,23] Furthermore, antibodies against GDH could cross-react with GDH produced by other anaerobic bacteria such as *Clostridium sporogenes*, *Peptostreptococcus anaerobius* and *Clostridium botulinum*.[24] In addition, the limited stability and high cost of antibodies remain as challenges.

Nucleic acid aptamers are synthetic single-stranded DNA or RNA molecules with a defined tertiary structure that can selectively bind to a target of interest. Remarkable progress has been made in aptamer research since the report of the first aptamers in 1990.[25,26] To date, numerous high affinity and highly specific aptamers have been identified against a broad range of targets such as metal ions, small organics, peptides, nucleic acids, proteins, viruses and whole cells.[27,28] In particular, aptamers possess several significant advantages over antibodies including low molecular weight, high stability, ease of synthesis and modification, and rapid folding properties.[29] Thus aptamers are promising alternatives to antibodies in many different applications, especially bioanalytical applications.[30-32]

SUMMARY

The present disclosure describes the selection and characterization of single-stranded DNA aptamers that specifically targeted glutamate dehydrogenase (GDH). After 10 rounds of selection, high-throughput sequencing was used to identify enriched aptamer candidates. Of 10 candidates, three aptamers for GDH were identified. Gel shift assays showed that these aptamers exhibited low nanomolar affinities. One aptamer was optimized based on structural analysis and further engineered into a structure-switching fluorescence signaling aptamer, wherein desorption from reduced graphene oxide (RGO) upon binding of GDH led to an increase in fluorescence emission. This method allowed for quantitative detection of GDH with a detection limit of 1 nM, providing great potential for its further application in *Clostridium difficile* infection diagnosis.

Accordingly, there are provided methods for the selection and characterization of aptamers as high-affinity specific recognition receptors for *C. difficile* GDH. In one embodiment, there is provided a DNA aptamer capable of binding to *C. difficile* GDH. In a particular embodiment, the aptamer that binds to *C. difficile* GDH comprises or consists of a sequence selected from the group consisting of SEQ ID NOS: 6, 8, 12, 16, 17, 18, 19, 20 and 21 or a functional fragment or modified derivative thereof. In an embodiment, the aptamer comprises or consists of a sequence selected from the group consisting of SEQ ID NO:6, 8 and 12; and the sequence further comprises SEQ ID NO:25 and SEQ ID NO:26 at the 5' and 3' ends respectively. In another embodiment, the aptamer comprises or consists of the sequence of SEQ ID NO: 16 or 17.

In another aspect, herein provided is an aptamer probe that comprises an aptamer disclosed herein and a detectable label. In an embodiment, the detectable label is at the 5' end of the sequence of the aptamer. In one embodiment, the detectable label comprises a fluorescent, a colorimetric or other optical probe or electrochemical moiety. In a particular embodiment, the detectable label is a fluorescent moiety, such as a fluorophore, optionally FAM.

In one embodiment, the aptamer probe comprises or consists of the sequence of SEQ ID NO: 5.

In yet another aspect, herein provided is a biosensor comprising an aptamer probe disclosed herein associated with a quencher molecule. In one embodiment, there is provided a biosensor comprising an aptamer probe disclosed herein adsorbed on a nanomaterial; wherein the aptamer changes conformation upon binding GDH and results in desorption from the nanomaterial. In an embodiment, the nanomaterial is reduced graphene oxide (RGO). In another embodiment, there is provided a biosensor comprising an aptamer probe disclosed herein in association with a quencher-oligonucleotide that quenches the detectable label; wherein the aptamer changes conformation upon binding GDH and results in release from the quencher such that the label is able to be detected. In some embodiments, the quencher-oligonucleotide is a DNA that hybridizes with the aptamer probe in the absence of GDH.

Also provided herein is a method for detecting the presence of *C. difficile* glutamate dehydrogenase in a test sample, comprising contacting said sample with an aptamer probe disclosed herein or a biosensor disclosed herein under conditions for a binding-induced conformational change in the aptamer to occur, and detecting a signal, wherein detection of a signal indicates the presence of *C. difficile* GDH in the test sample and lack of signal indicates that *C. difficile* GDH is not present.

The initial GDH screening test can be used in clinical diagnosis of CDI. Accordingly, further provided herein is a method of detecting *C. difficile* infection in a subject comprising testing a sample from the subject for the presence of *C. difficile* GDH by the method disclosed herein; and if GDH is present, further comprising testing the sample for the presence of *C. difficile* toxins A and B; wherein the presence of GDH and the presence of toxins indicates that the subject has a *C. difficile* infection. In an embodiment, testing for the presence of *C. difficile* toxins comprises a cell cytotoxicity neutralization assay, a toxin enzyme immunoassay or detection of toxin genes using PCR.

In another embodiment, the method further comprises treating the subject for *C. difficile* infection if GDH and toxins are present. Also provided is use of a medicament for treating *C. difficile* in a subject that has been identified as having a *C. difficile* infection by the method disclosed herein.

Even further provided herein is a kit for detecting *C. difficile* glutamate dehydrogenase, wherein the kit comprises the aptamer disclosed herein, the aptamer probe disclosed herein and/or the biosensor disclosed herein and instructions for use of the kit. In an embodiment, the kit further comprises a blocking agent for non-specific binding to the nanomaterial, such as bovine serum albumin, optionally at a concentration of 0.05 to 1%.

In yet a further aspect, herein provided is a method of identifying or producing an aptamer capable of binding to *C. difficile* glutamate dehydrogenase, wherein said method comprises (a) incubating a plurality of oligonucleotides in the presence of glutamate dehydrogenase, (b) collecting oligonucleotides that bind to the glutamate dehydrogenase, (c) amplifying said oligonucleotides of b) to yield a mixture of oligonucleotides enriched in nucleic acid sequences that are capable of binding to glutamate dehydrogenase; and (d) optionally, testing for binding to GDH. In an embodiment, the oligonucleotides include a primer region to allow for amplification and a random single stranded DNA sequence domain of about 40 nucleotides.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 shows a schematic illustration of the aptamer selection procedure.

FIG. 2 shows (A) binding affinity assay to identify aptamer sequences. The signal-to-background ratio (S/B) was defined as S/B=$I_1/I_0$, where $I_1$ and $I_0$ were the measured radioactive signal in the presence and absence of target rGDH. (B) Determination of the dissociation constants ($K_d$) for the identified aptamers against rGDH. The fraction of radioactivity in the shifted DNA band is calculated and plotted against the concentration of protein.

Figure 5:
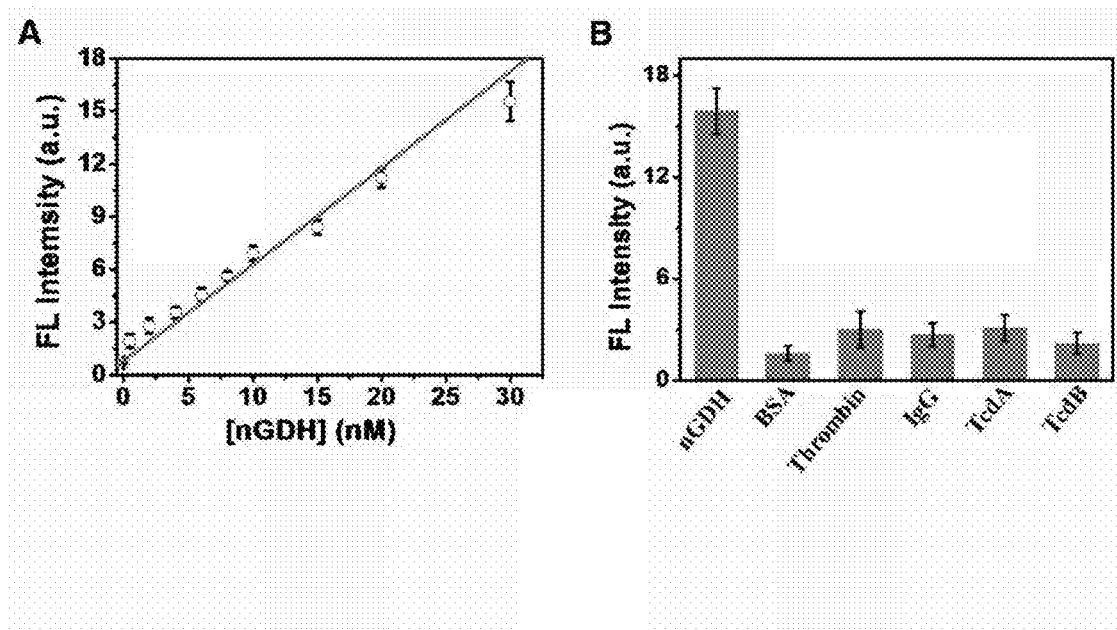

FIG. 5 shows (A) calibration curve of the aptasensor. The curve was plotted with the fluorescence intensity vs nGDH concentration. (B) Selectivity of the sensor for nGDH over other non-targeted proteins. The concentration of nGDH was 30 nM, and others were 300 nM each. The error bars represent the standard deviations of three parallel tests.

Figure 6:
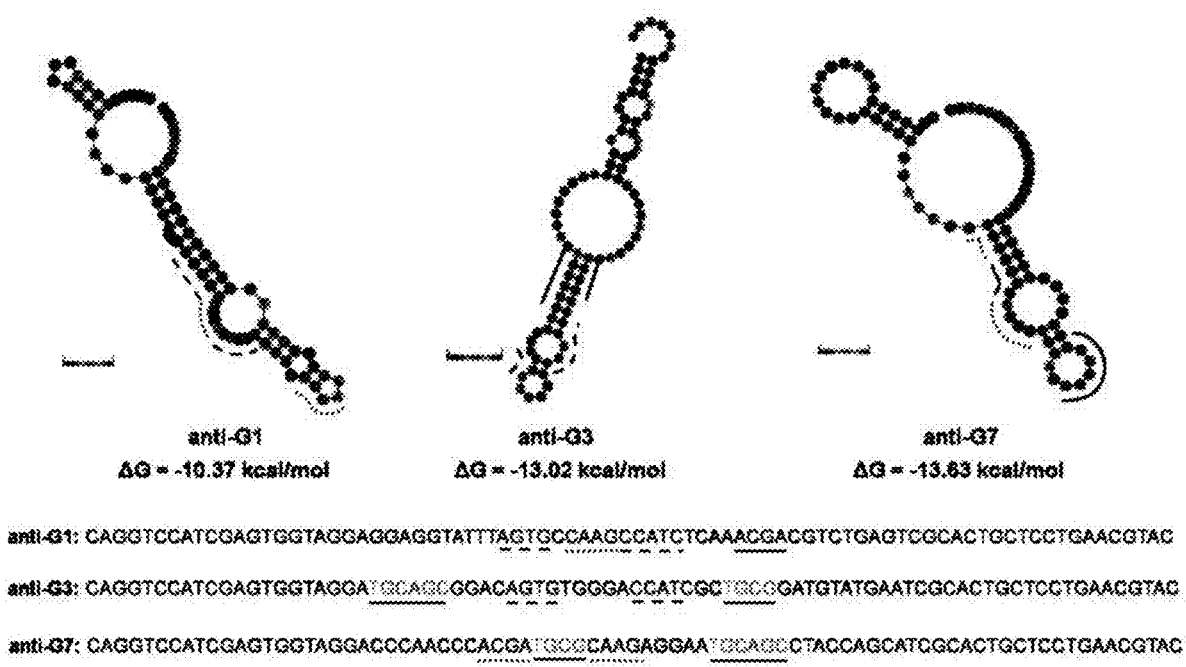

FIG. 6 shows secondary structures of the identified aptamers. The structure is configured by base-pairing probabilities with high (solid line), medium (dashed line) and low (dotted line) indicated. Anti-G1 sequence (SEQ ID NO:16); Anti-G3 sequence (SEQ ID NO:27) and Anti-G7 sequence (SEQ ID NO:28).

Figure 7:
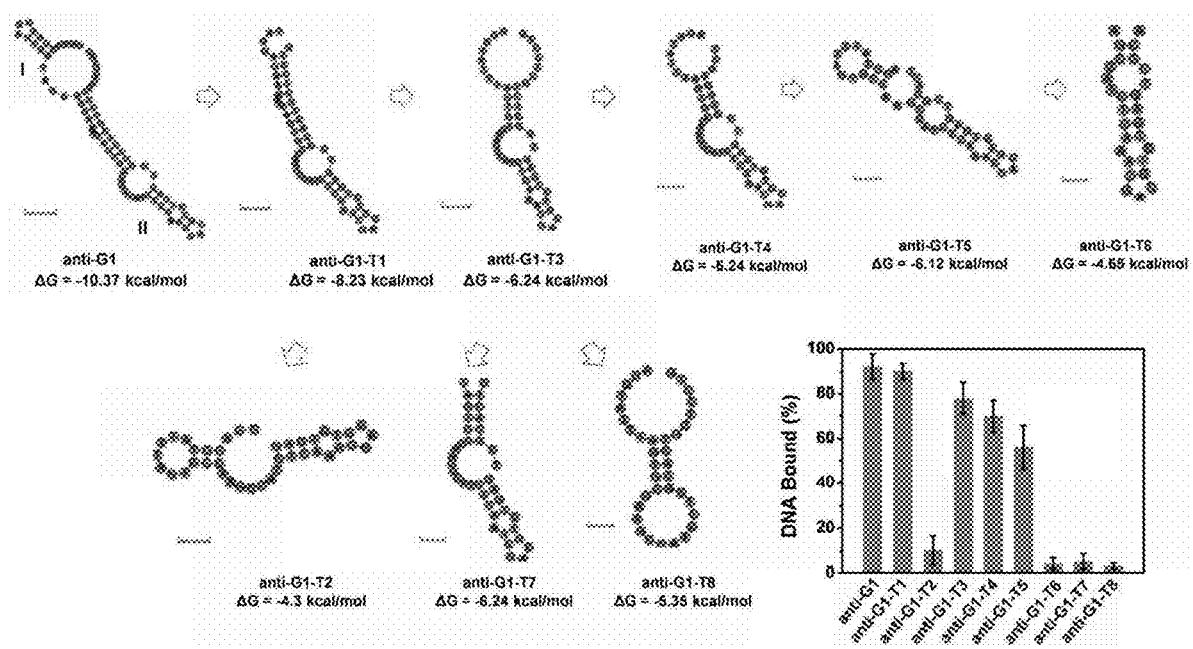

FIG. 7 shows the secondary structures of truncated sequences of anti-G1 and their bound percentage. The concentration of each truncated one is 20 nM.

Figure 8:
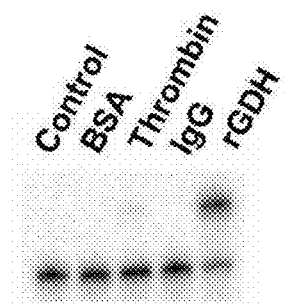

FIG. 8 shows a typical EMSA result for ant-GDH1-T1 aptamer in the presence of 10 nM BSA, thrombin, IgG and rGDH.

Figure 9:
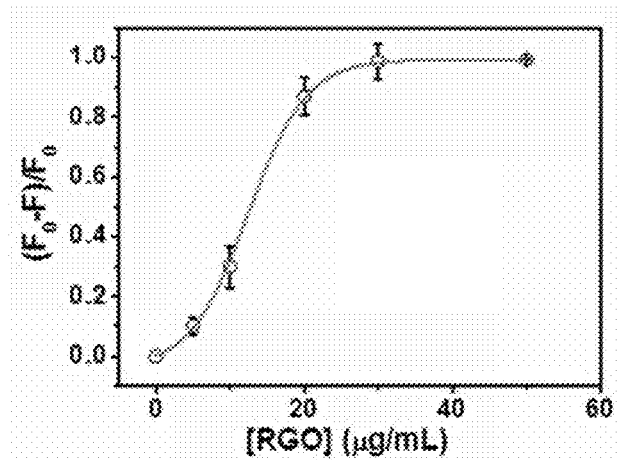

FIG. 9 shows the dependence of the quenching efficiency of anti-G1-T1 probe on RGO concentration after 30 min incubation in 1× binding buffer.

Figure 10:
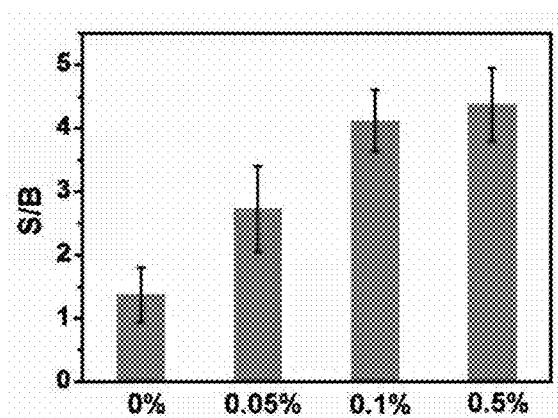

FIG. 10 shows the signal-to-background (S/B) ratios of RGO-aptamer sensor in the presence of different amounts of BSA.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The term "aptamer" as used herein refers to short, chemically synthesized, single stranded (ss) RNA or DNA oligonucleotides which fold into specific three-dimensional (3D) structures with dissociation constants in the pico- to nanomolar range. In general, aptamers may be single-stranded DNA or RNA, and may include modified nucleotides and/or nucleotide derivatives.

The term "nucleic acid molecule" and its derivatives, as used herein, are intended to include unmodified DNA or RNA or modified DNA or RNA. The nucleic acid molecules of the disclosure may contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

Examples of modified nucleotides which can be used to generate the nucleic acids disclosed herein include xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine. Alternatively, the nucleic acid molecules can be produced biologically using an expression vector.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506).

The term "DNA aptamer" as used herein refers to an aptamer comprising DNA or comprising modified backbone nucleic acids, such as PNA, that are derived from the DNA base sequence.

As used herein, "test sample" refers to a sample in which the presence of GDH of C. difficile are unknown and to be determined in an assay, preferably a diagnostic test. The test sample may be a "biological sample" comprising cellular and non-cellular material, including, but not limited to, tissue samples, blood, serum, other bodily fluids, and excrement, such as a stool sample from a subject, or an "environmental sample" obtained from water, soil or air.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "subject" as used herein includes all members of the animal kingdom including mammals such as a mouse, a rat, a dog and a human.

II. Aptamers, Probes and Biosensors of the Disclosure

In an embodiment, there is provided a DNA aptamer capable of binding to *C. difficile* GDH.

The term "GDH" or "glutamate dehydrogenase" as used herein refers to GDH from any source or organism. In an embodiment, the GDH is *C. difficile* GDH having a protein sequence as set out in Genbank Accession No. AAA62756.1 (SEQ ID NO:29).

In an embodiment, the aptamer interacts with and binds GDH through structural recognition. In an embodiment, the development of an aptamer that binds GDH is produced through Systematic Evolution of Ligands by EXponential enrichment (SELEX) technology.

In a particular embodiment, the aptamer that binds to *C. difficile* GDH comprises or consists of a sequence selected from the group consisting of SEQ ID NOS: 6, 8, 12, 16, 17, 18, 19, 20 and 21 or a functional fragment or modified derivative thereof.

The inventors identified three GDH aptamers in the high-throughput screening, G1, G3 and G7. Accordingly, in an embodiment, the aptamer comprises or consists of a sequence selected from the group consisting of SEQ ID NO:6, 8 and 12; and the sequence further comprises SEQ ID NO:25 and SEQ ID NO:26 at the 5' and 3' ends respectively.

Truncations of the G1 sequence were tested for binding to the aptamer and variants T1, T2, T3, T4 and T5 also showed binding to GDH. Accordingly, in another embodiment, the aptamer comprises or consists of SEQ ID NOs: 17, 18, 19, 20 or 21. Functional fragments of G3 and G7 would similarly be able to be obtained. The term "functional fragment" as used herein refers to the ability of the fragment to act as an aptamer to bind to GDH and change conformation upon the binding.

In one embodiment, the aptamer comprises or consists of the sequence of SEQ ID NO: 16 or 17. In another embodiment, the aptamer comprises or consists of SEQ ID NO: 27 or 28.

In another aspect, herein provided is an aptamer probe that comprises an aptamer disclosed herein and a detectable label. In an embodiment, the detectable label is at the 5' end of the sequence of the aptamer.

In one embodiment, the detectable label comprises a fluorescent, a colorimetric or other optical probe or electrochemical moiety. In a particular embodiment, the detectable label is a fluorescent moiety, such as a fluorophore.

The fluorophore may be any fluorophore, such as a chemical fluorophore, for example, one selected from fluorescein, rhodamine, coumarin, cyanine or derivatives thereof. In one embodiment, the detectable label is FAM or Cy5. The selection of the fluorophore is based upon one or more parameters including, but not limited to, (i) maximum excitation and emission wavelength, (ii) extinction coefficient, (iii) quantum yield, (iv) lifetime, (v) stokes shift, (vi) polarity of the fluorophore and (vii) size.

In one embodiment, the aptamer probe comprises or consists of the sequence of SEQ ID NO: 5.

In yet another aspect of the invention, a structure-switching signaling aptamer-based biosensor for real-time, sensitive and selective detection of GDH is disclosed. Accordingly, the present disclosure provides a biosensor comprising an aptamer probe disclosed herein associated with a quencher molecule; wherein the aptamer changes conformation upon binding to GDH and results in displacement of the quencher from the aptamer probe.

A quencher molecule is a substance with no native fluorescence and that absorbs the excitation energy from a fluorophore and dissipates the energy as heat, with no emission of fluorescence. Thus, when the fluorophore and quencher are close in proximity, the fluorophore's emission is suppressed.

In one embodiment, provided herein is a biosensor comprising an aptamer probe disclosed herein adsorbed on a nanomaterial; wherein the aptamer changes conformation upon binding GDH and results in desorption from the nanomaterial. In such an embodiment, the nanomaterial acts as a quencher molecule. In an embodiment, the nanomaterial may be any nanomaterial that is able to have nonspecific DNA binding affinity and allow target-induced binding, such as reduced graphene oxide (RGO) or metal particles, such as gold or platinum particles.

In an embodiment, the nanomaterial is reduced graphene oxide (RGO). In some embodiments, reduced graphene oxide is produced by reducing an aqueous solution of graphene oxide, prepared, for example as described in M. Liu, et al. ACS Nano 2012, 6, 3142-3151, with a reducing agent, such as ascorbic acid and ammonia, followed by heating, for example to about 80° C. to about 100° C. for about 3 to about 10 minutes. Cooling this solution to room temperature provides a stably dispersed RGO solution.

In an embodiment, the biosensor is comprised of a fluorometric aptamer probe adsorbed to the surface of reduced graphene oxide (RGO), wherein conformational changes in the aptamer induced by binding to GDH result in desorption of the aptamer probe from the RGO, to provide RGO and a GDH-aptamer probe complex that is detectable fluorometrically.

In an embodiment, the nanomaterial, such as RGO is blocked with a blocking agent to avoid non-specific binding, such as bovine serum albumin, milk or milk proteins. In an embodiment, the blocking agent is bovine serum albumin (BSA), optionally at a concentration of 0.05 to 1%.

The aptamer probes disclosed herein are also useful as part of a typical signaling structure-switching nucleic acid aptamer (FQDNA) biosensor system.

The term "structure-switching nucleic acid aptamers" or "reporter nucleic acid aptamers" as used herein refers to aptamer-based reporters that function by switching structures from a DNA/DNA or RNA/RNA complex to a DNA/target or RNA/target complex.

This general assay design is based on the change in conformation from a DNA/DNA duplex to a DNA/target complex. In this assay, an oligonucleotide is generated that contains an aptamer flanked by a primer region. A fluorophore-labeled oligonucleotide (FDNA) hybridizes to the primer region, while the quencher-labeled oligonucleotide (QDNA) hybridizes to the aptamer region. In the absence of target, this DNA/DNA duplex will be weakly fluorescent as a result of the close proximity of the quencher and fluorophore. Upon introduction of target, the aptamer forms a DNA/target complex, displacing the QDNA and producing a large increase in fluorescence intensity. The magnitude of signal generation is dependent upon the concentration of target added.

Accordingly, in another embodiment, there is provided a biosensor comprising an aptamer probe disclosed herein in association with a quencher-oligonucleotide that quenches the detectable label; wherein the aptamer changes conformation upon binding GDH and results in release from the quencher such that the label is able to be detected. In some embodiments, the quencher-oligonucleotide is a DNA that hybridizes with the aptamer probe in the absence of GDH.

In an embodiment, the quencher molecule is selected from dimethylaminoazobenzenesulfonic acid (dabcyl) and fluorescence resonance energy transfer (FRET or blackhole) quenchers and derivatives thereof.

III. Methods and Kits of the Disclosure

Also provided herein is a method for detecting the presence of C. difficile glutamate dehydrogenase in a test sample, comprising contacting said sample with an aptamer probe disclosed herein or a biosensor disclosed herein under conditions for a binding-induced conformational change in the aptamer to occur, and detecting a signal, wherein detection of a signal indicates the presence of C. difficile GDH in the test sample and lack of signal indicates that C. difficile GDH is not present.

In an embodiment, the test sample is a biological sample from a subject suspected of having a C. difficile infection. In one embodiment, the biological sample is a sample of excrement, for example, stool, from the subject.

The phrase "contacting said sample" refers to incubating the sample, which has been processed, with the aptamer probe, which allows any GDH in the sample to bind to the aptamer and induce a conformational change in the aptamer. In the biosensor disclosed herein, the aptamer-GDH is then desorbed from the nanomaterial and the fluorescent signal can be detected.

Detection of the signal can be performed using any available method, including, for example, colorimetric, electrochemical and/or spectroscopic methods, depending on the label on the aptamer. The detection can simply be detection of the direct product formed, for example, by reaction or interaction of the aptamer with GDH, if the product being formed possesses a color (or any signal, such as a fluorescent signal) that is intense enough to be detected and that is distinct from the color (or signal) of any of the starting reagents. In some embodiments, the detection means is not a separate component of the biosensor, but is instead formed during the assay and therefore is an inherent part of the biosensor. In a further embodiment, the detection means comprises a separate entity that reacts or interacts with the direct product formed by reaction of, for example, the aptamer and the GDH, the reaction with the separate entity resulting in a distinct detectable signal.

The initial GDH screening test can be used in clinical diagnosis of CDI. Accordingly, further provided herein is a method of detecting C. difficile infection in a subject comprising testing a sample from the subject for the presence of C. difficile GDH by the method disclosed herein; and if GDH is present, further comprising testing the sample for the presence of C. difficile toxins A and B (with a protein sequence as set out in Genbank Accession No. CAA63564.1 (SEQ ID NO:30) and CAA63562.1 (SEQ ID NO:31), respectively); wherein the presence of GDH and the presence of toxins indicates that the subject has a C. difficile infection. In an embodiment, testing for the presence of C. difficile toxins comprises a cell cytotoxicity neutralization assay, a toxin enzyme immunoassay or detection of toxin genes using PCR.

In another embodiment, the method further comprises treating the subject for C. difficile infection if GDH and toxins are present. Also provided is use of a medicament to treat a subject that has been identified as having a C. difficile infection by the method disclosed herein. In an embodiment, treatment of C. difficile or a medicament for treatment of C. difficile comprises antibiotics such as metronidazole, vancomycin or fidaxomicin.

Even further provided herein is a kit for detecting C. difficile glutamate dehydrogenase, wherein the kit comprises an aptamer disclosed herein, an aptamer probe disclosed herein and/or a biosensor disclosed herein and instructions for use of the kit. In an embodiment, the kit further comprises a blocking agent for non-specific binding to the nanomaterial, such as bovine serum albumin (BSA), milk or milk proteins. In an embodiment, the blocking agent is BSA, optionally at a concentration of 0.05 to 1%.

In yet a further aspect, herein provided is a method of identifying or producing an aptamer capable of binding to C. difficile glutamate dehydrogenase, wherein said method comprises (a) incubating a plurality of oligonucleotides in the presence of glutamate dehydrogenase, (b) collecting oligonucleotides that bind to the glutamate dehydrogenase, (c) amplifying said oligonucleotides of b) to yield a mixture of oligonucleotides enriched in nucleic acid sequences that are capable of binding to C. difficile glutamate dehydrogenase; and (d) optionally, testing for binding to C. difficile GDH. In an embodiment, the oligonucleotides include a primer region to allow for amplification and a random single stranded DNA sequence domain of about 40 nucleotides.

The following non-limiting examples are illustrative of the present application:

EXAMPLES

Figure 1:
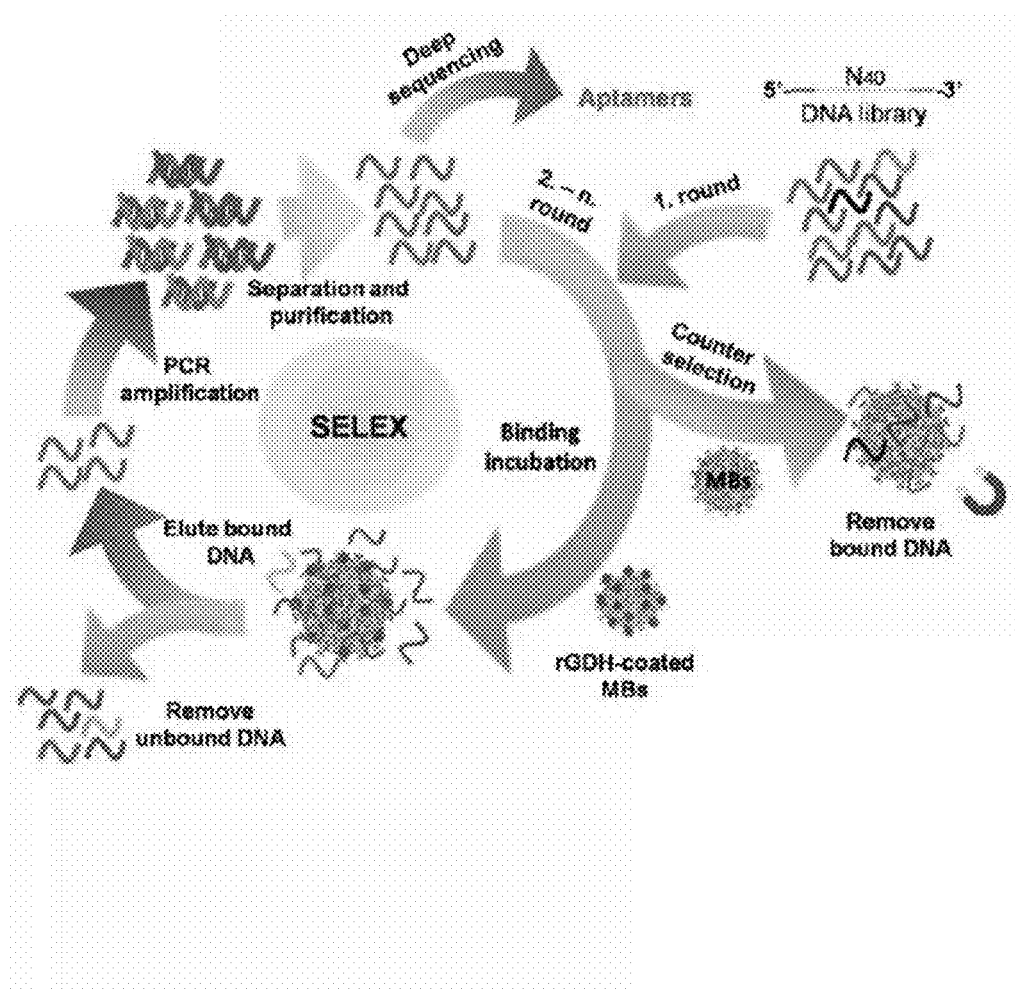

Results:

GDH testing has been used as an effective diagnostic tool for CDI, with a negative predictive value as high as 99%.[14,17,18] In the current study, using recombinant GDH (rGDH; the C. difficile GDH expressed and purified from E. coli) as a target, the SELEX method was performed to identify short synthetic DNA aptamers that could selectively bind this target with high affinity. The overall SELEX process is illustrated in FIG. 1. The initial ssDNA library contained a central random sequence of 40 nucleotides ($N_{40}$) flanked on each side by a constant sequence of 21 nucleotides that can function as primer binding sites for PCR. rGDH (46.8 KDa) containing a C-terminal $(His)_6$-tag was immobilized onto Ni-NTA magnetic beads to yield a selection matrix. To eliminate the non-specific DNA, the denatured DNA pool was first exposed to bare magnetic beads. In this counter-selection, DNA molecules that bound to beads were separated and discarded. The unbound DNA molecules were then collected and incubated with the selection matrix. After removal of the unbound sequences, the rGDH-bound DNA were eluted and amplified by PCR. The sense DNA was separated and purified by gel electrophoresis due to the fact that PCR products contained a primer with a spacer and an extension of 12 nucleotides. The recovered DNA (~100 pmol) was then used as input DNA for the next round of selection. A total of 10 selection rounds were completed, after which the sequences were analyzed from the DNA pools by high-throughput sequencing.

Figure 2:
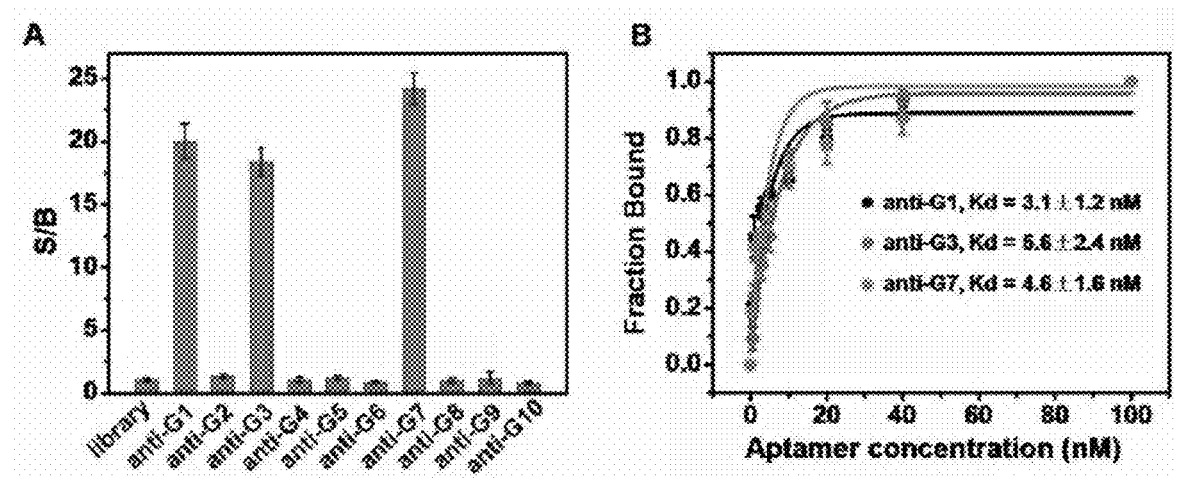

The sequencing results indicated an enrichment of aptamer candidate sequences. The total number of sequencing reads was about 6 million. Among these, the top 10 highest multiplicity sequences for rGDH represented 17% of the selected pools (Table 1). To rapidly identify the selected sequences with high affinities, each of the 10 sequenced aptamer candidates were labeled with $\gamma$-$[_{32}P]$-ATP, and tested each for its ability to bind to rGDH immobilized on magnetic beads using the original SELEX conditions. Binding assays carried out for each sequence against uncoated beads were used as negative controls. As shown in FIG. 2A, the initial DNA library did not yield any obvious signal above background levels (S/B). However, anti-GDH1, anti-GDH3 and anti-GDH7 showed high binding affinity for rGDH. By performing rGDH binding assays the equilibrium dissociation constants ($K_d$) were calculated in the low nanomolar range (FIG. 2B). The lowest $K_d$ of 3.1±1.2 nM was obtained for anti-GDH1. For anti-GDH3 and anti-GDH7, the Kd values were determined to be 5.6±2.4 nM and 4.6±1.6 nM, respectively. These affinities were in accordance with previous studies on aptamers targeting diverse proteins, such as human thrombin,[33] human platelet-derived growth factor (PDGF),[34] human immunoglobulin E (IgE),[35] and streptavidin,[36] with $K_d$ values in the low nanomolar range. To understand the structural differences between the aptamers, the theoretical secondary structures were estimated using a dynamic programming algorithm of lowest free energy.[37] Typical stem-loop motifs were found in their secondary structures (FIG. 6).

It is well-known that not all of the nucleotides play an important role in the aptamer-target binding reaction. An aptamer usually contains nucleotides that either bind to the target or facilitate the binding.[38] To determine the key nucleotides in the anti-GDH aptamer, truncated versions were produced based on the secondary structure of the anti-GDH1 aptamer (Table 2), in which stem-loop structure (I) at the 5' end and a non-pairing region at the 3' end were removed to yield the 59 nucleotide variant—T1. This variant could bind rGDH-coated beads with a bound percentage of 90±4% (FIG. 7), similar to the full-length aptamer. T1 was further shortened by deleting the primers region, leaving the random sequence of 40 nucleotides in variant T2. However, this truncation resulted in a significant loss of binding ability, i.e. weakly active (10±6%), implying that the stem formed between the random sequence and part of the primer region was essential for maintaining the binding conformation. Removing the G-rich part at the 5' end of the T1 variant decreased the binding ability (T3; 78±7%), indicating that the G-rich region could be of importance for protein binding through the formation of advanced tertiary structures. If the CCTG sequence at the 3' end of T3 was deleted, it was observed that this truncated version (T4) retained similar binding affinity for rGDH (70±7%). However, further removal of the GCT sequence at the 3' end of T4 causes a change in the secondary structure (T5) and decreased its binding affinity (56±9%), indicating the primary role of the non-pairing region in T4 for binding. Furthermore, there was no obvious binding for T6 (4±3%) if the overhanging motif at the 5' end of T5 was deleted. Strikingly, in construct T3 the non-pairing region was deleted to obtain variant T7. This resulted in the complete loss of the binding ability (5±4%), confirming that the recognition between anti-GDH1 and rGDH was dominantly controlled by the non-pairing region in T3. Finally, the entire motif II was removed and the remaining loop was closed in T3 (T8). It was observed that this variant lost its binding affinity to rGDH (3±1%), suggesting, without wishing to be bound by theory, that the terminal stem-loop section of T3 was critical for keeping the secondary structure for binding.

Figure 3:
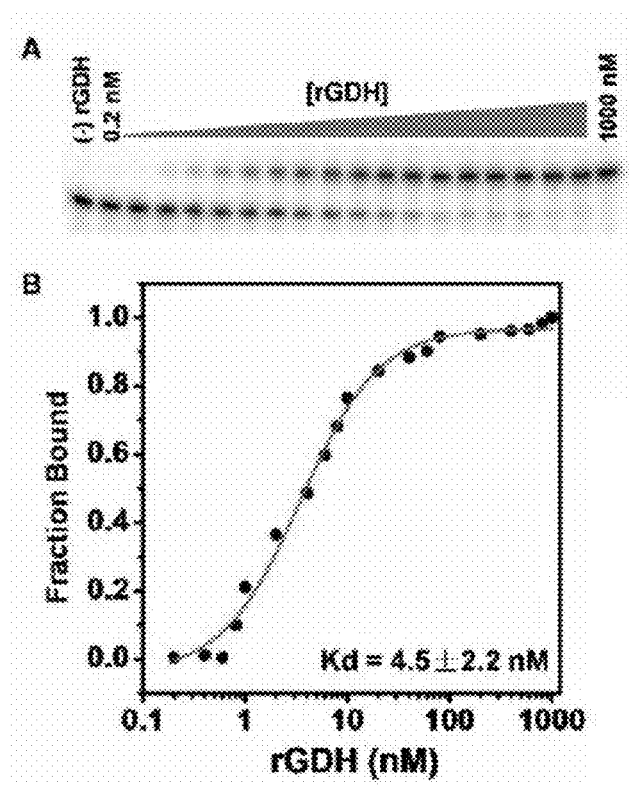
FIG. 3 shows (A) typical EMSA result for anti-GDH1-T1 aptamer binding to rGDH, and the corresponding binding curve (B).

The truncated aptamer, anti-GDH-T1, was then radioactively labeled at the 5' end and tested for binding to the rGDH target by EMSA assays.[39,40] A typical image of an EMSA result is shown in FIG. 3A. It was observed that the electrophoretic mobility of the protein-aptamer complex was typically less than that of the free aptamer. The fractional saturation of bound aptamer was calculated as a function of rGDH concentration (FIG. 3B). A $K_d$ value of 4.5±2.2 nM was determined for the anti-GDH1-T1 aptamer, indicating its high-affinity. The specificity was also tested by EMSA. No obvious band was observed when using proteins such as BSA, thrombin and IgG (FIG. 8).

The anti-GDH1-T1 aptamer was then used to produce a fluorescence-based biosensor for detecting native GDH from *C. difficile* (nGDH). Biosensing by fluorescence has attracted much attention in the design of various aptasensors, largely due to its simplicity and sensitivity.[41,42] A structure-switching approach for engineering signaling aptamers that functioned by switching structures from DNA-DNA duplex to aptamer-target complex was previously reported.[43] The presence of target triggers the release of a quencher-labeled complementary DNA strand from the fluorophore-labeled aptamer, accompanied by an increase of fluorescence intensity because of fluorescence dequenching. In spite of the general utility of the strategy, fine-tuning of the complementary DNA remains a major challenge as many sequences must be rationally designed and tested to make sure that the signaling aptamers undergo a significant conformational change upon target binding. Therefore, to overcome this problem, the aptamer was coupled to graphene-based nanomaterials, due to the fact that: (1) the π-rich conjugation domains allow graphene to directly interface with DNA through non-covalent π-π stacking interaction;[44] (2) graphene produces highly efficient fluorescence quenching based on energy transfer or electron transfer mechanisms.[45,46]

Figure 4:
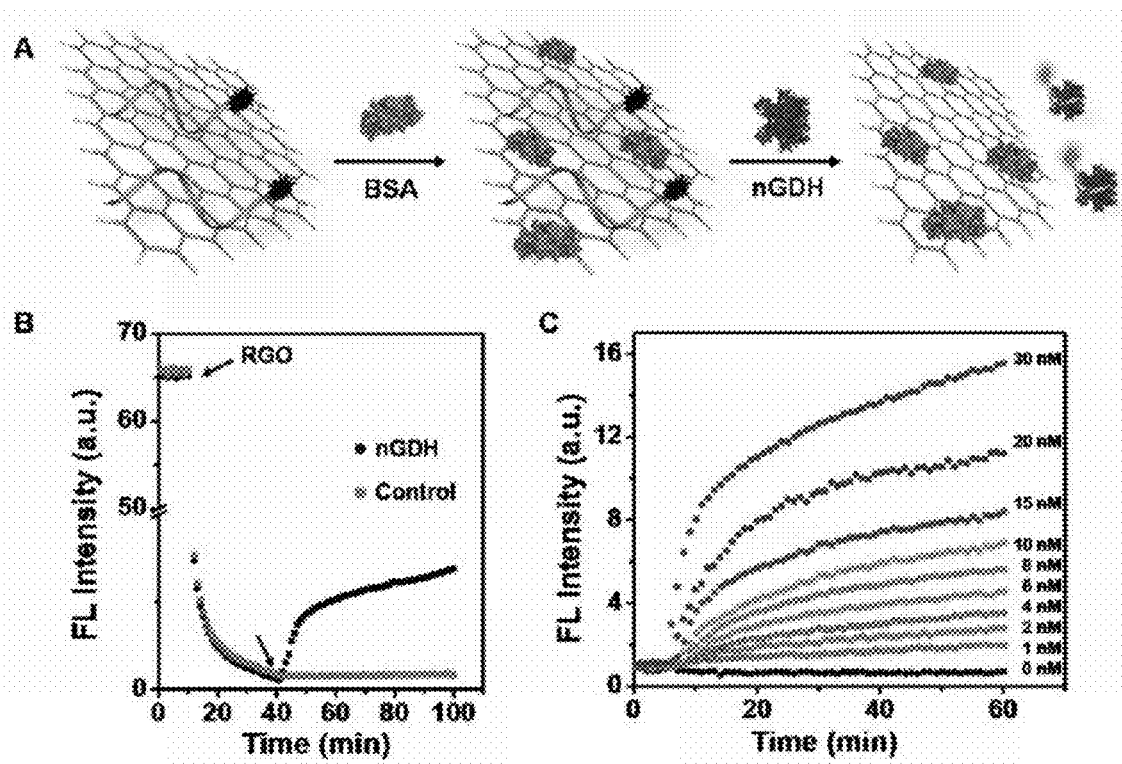
FIG. 4 shows functionalization of RGO with aptamers. (A) Schematic illustration of the RGO-aptamer system for nGDH detection. (B) The kinetic response of RGO-aptamer sensor to sequential addition of 30 µg/mL RGO and nGDH (100 nM) in binding buffer. (C) Time-dependent fluorescence response with varying concentrations of nGDH. $\lambda_{ex}/\lambda_{em}$=494/518 nm.

The working principle and key functionalities of the aptamer-graphene biosensor are schematically illustrated in FIG. 4A. First, the structure-switching signaling aptamer-graphene construct was obtained by non-covalent self-assembly of a fluorophore-labeled anti-GDH-T1 aptamer onto the surface of RGO in solution. Then the free sites in RGO were blocked by BSA in order to minimize the nonspecific binding of GDH onto the RGO surface. Upon recognition and binding of specific targets by the adsorbed aptamers, the conformational switch of the bound aptamers occurred in conjunction with the desorption of the weakly binding aptamer-target complex from the RGO surface,[47] which immediately recovered the fluorescence signal. Thus the target recognition event was efficiently converted into a measurable signal, providing a powerful analytical sensing system.

To validate the feasibility of the proposed sensing method, a kinetic study was carried out to record the time-dependent fluorescence changes of aptamers upon introduction of the GDH target (FIG. 4B). As expected, the fluorescence intensity was initially quenched upon addition of the aptamer to RGO (it is noteworthy that an experiment with varying concentrations of RGO was conducted to ensure the complete fluorescence quenching of aptamers; see FIG. 9). In direct contrast, when nGDH was added, the fluorescence intensity was restored, and increased as a function of reaction time. This result suggested a conformational change of the aptamer upon binding to target, which would weaken the interaction between the aptamer probe and RGO, thereby causing desorption and/or causing the fluorescence probe in weakly bound aptamers to move away from the RGO surface, hindering the energy transfer or electron transfer process. After 1 h incubation, a fluorescence enhancement of more than 14-fold was obtained.

Since graphenes can also function as a scaffold for binding protein through electrostatic interactions, hydrophobic interactions or aromatic π-π stacking,[48] minimizing the free surface binding sites to avoid the nonspecific binding of nGDH on RGO surface was carried out. With the aim of studying the effect of blocking agent on the sensor response, a treatment of the system was carried out with different concentrations of BSA. The signal response quantified as signal-to-background (S/B) ratios increased with increased amount of BSA from 0.05% to 0.5% (FIG. 10). This result suggested that the blocking procedure was necessary to remove the unspecific binding sites on the RGO surface. As noted, this method presented here could open new opportunities for improving the performance of graphene-aptamer based fluorescent biosensors.[49-51]

To demonstrate the sensitivity of the proposed biosensor for the detection of nGDH, a kinetic study was carried out to record the time-dependent fluorescence changes upon the addition of various amounts of nGDH. As shown in FIG. 4C, the kinetics of the fluorescence enhancement and the end-point intensity (at 60 min) was dependent on the nGDH concentrations. The detection limit (defined as 3σ/slope, with σ being the standard deviation of the blank samples) of the sensor was determined to be 1 nM (FIG. 5A). The selectivity of the aptamer-graphene biosensing system was also evaluated by using non-target proteins (BSA, thrombin, IgG, TcdA and TcdB). As shown in FIG. 5B, no significant response was observed even when the concentration of each non-target protein was in 10-fold excess of nGDH, indicating the high selectivity of the developed aptasensor.

Materials and Methods

Chemicals and Reagents

All DNA oligonucleotides were obtained from Integrated DNA Technologies (IDT), and purified by standard 10% denaturing (8 M urea) polyacrylamide gel electrophoresis (dPAGE). The sequences of the random oligonucleotides and primers were as follows: DNA library, 5'-CAG GTC CAT CGA GTG GTA GGA-$N_{40}$-TCG CAC TGC TCC TGA ACG TAC-3' (SEQ ID NO: 1); forward primer (FP), 5'-CAG GTC CAT CGA GTG GTA GGA-3' (SEQ ID NO: 2); reverse primer 1 (RP1), 5'-GTA CGT TCA GGA GCA GTG CGA-3' (SEQ ID NO: 3); reverse primer 2 (RP2), 5'-AAA AAA AAA AAA/iSpC3/GTA CGT TCA GGA GCA GTG CGA-3' (SEQ ID NO: 4); FAM-labeled anti-GDH1-T1: 5'-FAM-TAG GAG GAG GTA TTT AGT GCC AAG CCA TCT CAA ACG ACG TCT GAG TCG CAC TGC TCC TG-3' (SEQ ID NO: 5). Two versions of GDH proteins were used in this study: recombinant (his-tagged) glutamate dehydrogenase (rGDH; expressed and purified from *E. coli* cells), and native GDH (nGDH; directly purified from *C. difficile* cells), both of which were obtained from Pro-Lab Diagnostics (Toronto, Canada). TcdA and TcdB proteins from *C. difficile* were also provided by Pro-Lab Diagnostics. Human immunoglobulin G (IgG) and human thrombin were obtained from Sigma. *Thermus thermophilus* DNA polymerase was obtained from Biotools. γ-[$^{32}$P]-ATP was purchased from Perkin Elmer. Adenosine 5'-triphosphate (ATP), dNTPs and T4 polynucleotide kinase (PNK) were purchased from MBI Fermentas. Ni-NTA magnetic agarose beads were obtained from QIAGEN. All other chemicals and solvents were purchased from Sigma and used without further purification. Water was purified with a Milli-Q Synthesis A10 water purification system.

In Vitro Selection of Aptamers

The SELEX procedure was performed according to a previously reported method with minor modifications, and is shown in FIG. 1.[52] rGDH-bound Ni-NTA magnetic beads were first prepared by incubating 100 µL of a 5% (w/v) suspension of Ni-NTA magnetic agarose beads (Qiagen) and 10 µL of rGDH (2.3 mg/mL) in 1× binding buffer (1×PBS, containing 150 mM NaCl and 0.02% Tween-20, pH 7.6) with a final volume of 500 µL. After mixing with rotation for 1 h at 4° C., the rGDH-coated beads were washed three times with binding buffer, re-suspended and stored in 500 µL binding buffer at 4° C.

For the initial round of SELEX, 20 µM of DNA library, which was denatured at 95° C. for 5 min and immediately cooled on ice for 10 min, was first counter-selected against 20 µL of a 5% suspension of Ni-NTA magnetic beads in 500 µL of 1× binding buffer in order to reduce non-specifically bound DNA molecules. Then the remaining unbound DNA library was exposed to 100 µL of bead-bound rGDH with rotation in 500 µL 1× binding buffer at room temperature. After incubating for 30 min, the beads were magnetically trapped and washed three times with binding buffer to remove the unbound DNA. Subsequently, target-bound aptamers were eluted by incubating the recovered beads with 300 µL of elution buffer (1× binding buffer containing 500 mM imidazole) at 37° C. for 20 min with gentle shaking. After recovery by ethanol precipitation, the obtained DNA was amplified by PCR1. Each PCR mixture (50 µL) contained the DNA template prepared above, 1 µM FR, 1 µM RP1, 200 µM dNTPs, 1×PCR reaction buffer (75 mM Tris-HCl, pH 9.0, 2 mM $MgCl_2$, 50 mM KCl, 20 mM $(NH_4)_2SO_4$) and 2.5 U *Thermus thermophilus* DNA polymerase. Thermal cycles were typically performed as follows: 94° C. for 30 s; 16 cycles of 94° C. for 30 s, 50° C. for 45 s and 72° C. for 40 s; 72° C. for 5 min. An agarose gel (3%) electrophoresis was performed to check the PCR1 product. In order to separate the relevant DNA strands from the double-stranded PCR1 products, the above PCR1 product was used as the template for PCR2 using primers FR and RP2 while following the same protocol as for PCR1. During this process, the hexaethyleneglycol spacer in RP2 can prevent the amplification of the A12 fragment, thus making the nonaptamer-coding DNA strand 12 nucleotides longer than the coding strand. The DNA aptamers were separated and purified by 10% dPAGE (8 M urea), and used as the ssDNA library for the next round. After 10 rounds of selection, 100 nM of purified PCR1 product that contained a unique 6 nt barcode was subjected to deep sequencing using the MiSeq (Illumina) sequencing platform.

Characterization

Time-dependent fluorescence emission measurements were performed using a Cary Eclipse fluorescence spectrophotometer (Varian) with an excitation wavelength of 494 nm and emission wavelength of 518 nm. The bandpasses for excitation and emission were set at 5 nm/5 nm and photomultiplier tube voltage was 600 V. Fluorescence data was typically collected every 1 min over a period of 60 min. Both the phosphorimage and fluorimage of gels were obtained using a Typhoon 9200 variable mode imager (GE Healthcare) and analyzed by ImageQuant software (Molecular Dynamics).

Identification of High-Affinity Aptamers for rGDH

To evaluate the binding characteristics of all sequenced aptamers, the SELEX procedure was performed as described above. Briefly, the aptamer candidates were first labeled with γ-[$^{32}$P]-ATP at the 5' end by using T4 polynucleotide kinase according to the manufacturer's protocol, and purified by 10% dPAGE (8 M urea). Then 100 nM aptamer candidate was incubated with 100 µL rGDH-coated beads at room temperature for 30 min in a total volume of 500 µL 1× binding buffer with gentle rotation. In parallel, negative controls consisting of the aptamer incubated with uncoated beads were included. Following several washing steps, the bound ssDNA in the reaction mixtures were analyzed by 10% dPAGE.

To determine the binding affinity of identified aptamers towards rGDH, binding assays were conducted in 500 µL of 1× binding buffer containing a fixed number of bead-bound rGDH (100 µL) and radioactively-labeled aptamers in a range of concentrations (0 nM to 100 nM). Uncoated beads were used as a negative control for nonspecific binding in each experiment. The apparent dissociation constants (IQ)

of each aptamer were obtained by fitting the fractional bound DNA to the total aptamer concentration using a one-site binding model.

Electrophoretic Mobility Shift Assays (EMSA)

Binding reactions were performed in 20 μL of 1× binding buffer containing 3 nM 32P-labeled anti-GDH1-T1 aptamer and various concentrations of rGDH (0 to 1000 nM). After incubation for 30 min, the reaction mixtures were spiked with 6× loading buffer, and then loaded into the wells of a nondenaturing polyacrylamide gel (8%) at 4° C. Visualization of DNA bands was done using a Typhoon 9200 imager and the resulting bands were quantified with ImageQuant software.

Procedure for nGDH Assay

In a typical assay, 20 μL of 5× binding buffer (5×PBS, containing 750 mM NaCl and 0.1% Tween-20, pH 7.6), 2 μL of FAM-labeled (5' end) aptamer probe (7 μM), 30 μL of RGO solution (100 μg/mL) and 48 μL of water were first mixed and incubated in a micro-centrifuge tube for 30 min. Then, 10 μL of 1% BSA was added to block the surface. After incubating for 20 min, 5 μL of nGDH with different dilutions was added to the mixture and time-dependent fluorescence emission measurements were performed at $\lambda_{ex}/\lambda_{em}$=494/518 nm. The emission intensity obtained at a reaction time of 60 min was plotted against nGDH concentration to obtain a limit of detection. A similar experiment was carried out using non-target proteins (BSA, human thrombin, human IgG, TcdA and TcdB from *C. difficile*) to evaluate aptamer selectivity.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1 the high-throughput sequencing results from selection rounds 10 pools for target rGDH

| ID | Sequence of random region (5'→3') | Multiplicity | % of Total | SEQ ID NO: |
|---|---|---|---|---|
| anti-G1 | GGAGGTATTTAGTGCCAAGCCATCTCAAACG ACGTCTGAG | 138479 | 2.2296 | SEQ ID NO: 6 |
| anti-G2 | CCGAGTTCCCAATATTATGGCTATGCAGGATA CTTCACCT | 122299 | 1.9691 | SEQ ID NO: 7 |
| anti-G3 | TGCAGCGGACAGTGTGGGACCATCGCTGCG GATGTATGAA | 113617 | 1.8293 | SEQ ID NO: 8 |
| anti-G4 | TGAGTACTAGTTCCCCAGGAGAAAGCAGAT CCCCAGGTAC | 104786 | 1.6872 | SEQ ID NO: 9 |
| anti-G5 | GCACAGGACGCAAGATGAATGCAGCATACC AGTCCCTAGA | 101800 | 1.6391 | SEQ ID NO: 10 |
| anti-G6 | CAGCTGTCGACGCGTTACCGTGAACGGAAC ACCGATGACG | 98143 | 1.5802 | SEQ ID NO: 11 |
| anti-G7 | CCCAACCCACGATGCGCAAGAGGAATGCAG CCTACCAGCA | 98046 | 1.5786 | SEQ ID NO: 12 |
| anti-G8 | TGCGTGATTGGACCAGGGAAAGATGCACCG CAAGACAAGA | 96909 | 1.5603 | SEQ ID NO: 13 |
| anti-G9 | AGGATAATCCGATACGCAAGAAGAAAGCAG ATTACCAGGA | 94805 | 1.5265 | SEQ ID NO: 14 |
| anti-G10 | CAAAGTCGGCAAGGTGGAAAGCAGCCACAC CACGACTAGT | 88684 | 1.4279 | SEQ ID NO: 15 |

Note:
Each sequence also contains CAGGTCCATC GAGTGGTA (SEQ ID NO: 25) at the 5' end and TCGCACTGCT CCTGAACGTA C (SEQ ID NO: 26) at 3'end.

TABLE 2 the truncated aptamer sequences

| ID | Sequence (5'→3') | SEQ ID NO: |
|---|---|---|
| anti-G1 | CAGGTCCATCGAGTGGTA<u>GGAGGAGGTATTTAGTGCCAAGCCATCTCAA ACGACGTCTGAG</u>TCGCACTGCTCCTGAACGTAC | SEQ ID NO: 16 |
| anti-G1-T1 | TA<u>GGAGGAGGTATTTAGTGCCAAGCCATCTCAAACGACGTCTGAG</u>TCGC ACTGCTCCTG | SEQ ID NO: 17 |

TABLE 2-continued the truncated aptamer sequences

| ID | Sequence (5'→3') | SEQ ID NO: |
|---|---|---|
| anti-G1-T2 | *GGAGGAGGTATTTAGTGCCAAGCCATCTCAAACGACGTCTGAG* | SEQ ID NO: 18 |
| anti-G1-T3 | *AGGTATTTAGTGCCAAGCCATCTCAAACGACGTCTGAG*TCGCACTGCTCCTG | SEQ ID NO: 19 |
| anti-G1-T4 | *AGGTATTTAGTGCCAAGCCATCTCAAACGACGTCTGAG*TCGCACTGCT | SEQ ID NO: 20 |
| anti-G1-T5 | *AGGTATTTAGTGCCAAGCCATCTCAAACGACGTCTGAG*TCGCACT | SEQ ID NO: 21 |
| anti-G1-T6 | *AGCCATCTCAAACGACGTCTGAG*TCGCA | SEQ ID NO: 22 |
| anti-G1-T7 | *TAGTGCCAAGCCATCTCAAACGACGTCTGAG*TCGCACTG | SEQ ID NO: 23 |
| anti-G1-T8 | *AGGTATTTAGTGCCAAGCCATCG*TCGCACTGCTCCTG | SEQ ID NO: 24 |

Note:
Nucleotides in the original random-sequence domain are shown in italic and underlined.

FULL CITATIONS FOR DOCUMENTS
REFERRED TO IN THE APPLICATION

1. Stoddart, B.; Wilcox, M. H. *Curr. Opin. Infect. Dis.* 2002, 15, 513-518.
2. Bartlett, J. G. *Clin. Infect. Dis.* 1994, 18, 265-272.
3. Lyerly, D. M.; Krivan, H. C.; Wilkins, T. D. *Clin. Microbiol. Rev.* 1988, 1, 1-18.
4. McFarland, L. V.; Stamm, W. E. *Am J Infect Control* 1986, 14: 99-109.
5. Gravel, D.; Miller, M.; Simor, A.; Taylor, G.; Gardam, M.; McGeer, A.; Hutchinson, J.; Moore, D.; Kelly, S.; Boyd, D.; Mulvey, M. the Canadian Nosocomial Infection Surveillance Program. *Clin. Infect. Dis.* 2009, 48, 568-576.
6. Rupnik, M.; Wilcox, M. H.; Gerding, D. N. *Nat. Rev. Microbiol.* 2009, 7, 526-536.
7. Vonberg, R. P.; Reichardt, C.; Behnke, M.; Schwab, F.; Zindler, S.; Gastmeier, P. *J. Hosp. Infect.* 2008, 70, 15-20.
8. Kelly, C. P.; LaMont, J. T. *Annu. Rev. Med.* 1998, 49, 375-390.
9. Arroyo, L. G.; Rousseau, J.; Willey, B. M.; Low, D. E.; Staempfli, H.; McGeer, A.; Weese, J. S. *J. Clin. Microbiol.* 2005. 43, 5341-5343.
10. Peterson, L. R.; Kelly, P. J.; Nordbrock, H. A. *Eur. J. Clin. Microbiol. Infect. Dis.* 1996, 15, 330-336.
11. Kelly, C. P.; Pothoulakis, C.; LaMont. J. T. *N. Engl. J. Med.* 1994, 330, 257-262.
12. Planche, T.; Aghaizu, A.; Holliman, R.; Riley, P.; Poloniecki, J.; Breathnach, A.; Krishna, S. *Lancet Infect. Dis.* 2008, 8, 777-784.
13. Barbut, F.; Braun, M.; Burghoffer, B.; Lalande, V.; Eckert, C. *J. Clin. Microbiol.* 2009, 47, 1276-1277.
14. Carroll, K. C. *Anaerobe* 2011, 17, 170-174.
15. Shetty, N.; Wren, M. W. D.; Coen, P. G. *J. Hosp. Infect.* 2011, 77, 1-6.
16. Goldenberg, S. D.; Gumban, M.; Hall, A.; Patel, A.; French, G. L. *Diagn. Microbiol. Infect. Dis.* 2011, 70, 417-419.
17. Zheng, L.; Keller, S. F.; Lyerly, D. M.; Carman, R. J.; Genheimer, C. W.; Gleaves, C. A.; Kohlhepp, S. J.; Young, S.; Perez, S.; Ye, K. *J. Clin. Microbiol.* 2004, 42, 3837-3840.
18. Fenner, L.; Widmer, A. F.; Goy, G.; Rudin, S.; Frei, R. *J. Clin. Microbiol.* 2008, 46, 28-30.
19. Goldenberg, S. D.; Cliff, P. R.; Smith, S.; Milner, M.; French, G. L. *J. Hosp. Infect.* 2010, 74, 48-54.
20. Kawada, M.; Annaka, M.; Kato, H.; Shibasaki, S.; Hikosaka, K.; Mizuno, H.; Masuda, Y.; Inamatsu, T. *J. Infect. Chemother.* 2011, 17, 807-811.
21. Cohen, S. H.; Gerding, D. N.; Johnson, S.; Kelly, C.; Loo, V. G.; McDonald, L. C.; Pepin, J.; Wilcox, M. H. *Infect. Control Hosp. Epidemiol.* 2010, 31, 431-455.
22. Eastwood, K.; Else, P.; Charlett, A.; Wilcox, M. *J. Clin. Microbiol.* 2009, 47, 3211-3217.
23. Tenover, F. C.; Baron, E. J.; Peterson, L. R.; Persing, D. H. *J. Mol. Diagn.* 2011, 13, 573-582.
24. Wilkins, T. D.; Lyerly, D. M. *J. Clin. Microbiol.* 2003, 41, 531-534.
25. Tuerk, C.; Gold, L. *Science* 1990, 249, 505-10.
26. Ellington, A. D.; Szostak, J. W. *Nature* 1990, 346, 818-22.
27. Shamah, S. M.; Healy, J. M.; Cload, S. T. *Acc. Chem. Res.* 2008, 41, 130-138.
28. Cho, E. J.; Lee, J. W.; Ellington, A. D. *Annu. Rev. Anal. Chem.* 2009, 2, 241-264.
29. Mascini, M.; Palchetti, I.; Tombelli, S. *Angew. Chem. Int. Ed.* 2012, 51, 1316-1332.
30. Hamula, C. L. A.; Guthrie, J. W.; Zhang, H.; Li, X. F.; Le, X. C. *Trac-Trends Anal. Chem.* 2006, 25, 681-691.
31. Sefah, K.; Phillips, J. A.; Xiong, X. L.; Meng, L.; Van Simaeys, D.; Chen, H.; Martin, J.; Tan, W. H. *Analyst* 2009, 134, 1765-1775.
32. Iliuk, A. B.; Hu, L.; Andy Tao, W. *Anal. Chem.* 2011, 83, 4440-4452.
33. Tasset, D. M.; Kubik, M. F.; Steiner, W. *J. Mol. Biol.* 1997, 272, 688-698.
34. Green, L. S.; Jellinek, D.; Jenison, R.; Ostman, A.; Heldin, C. H.; Janjic, N. *Biochemistry* 1996, 35, 14413-14424.
35. Mendonsa, S. D.; Bowser, M. T. *Anal. Chem.* 2004, 76, 5387-5392.
36. Oh, S. S.; Ahmad, K. M.; Cho, M.; Kim, S.; Xiao, Y.; Soh, H. T. *Anal. Chem.* 2011, 83, 6883-6889.
37. Gruber, A. R.; Lorenz, R.; Bernhart, S. H.; Neuboock, R.; Hofacker, I. L. *Nucleic Acids Res.* 2008, 36, W70-W74.
38. Galas, D. J.; Schmitz, A. *Nucleic Acids Res.* 1978, 5, 3157-3170.
39. Hellman, L. M.; Fried, M. G. *Nat. Protoc.* 2007, 2, 1849-1861.
40. Ferber, M. J.; Maher, *J. Anal. Biochem.* 1997, 244, 312-320.

41. Nutiu, R.; Li, Y. *Chem. Eur. J.* 2004, 10, 1868-1876.
42. Nutiu, R.; Li, Y. *Methods* 2005, 37, 16-25.
43. Nutiu, R.; Li, Y. *J. Am. Chem. Soc.* 2003, 125, 4771-4778.
44. Varghese, N.; Mogera, U.; Govindaraj, A.; Das, A.; Maiti, P. K.; Sood, A. K.; Rao, C. N. R. *Chem Phys Chem* 2009, 10, 206-210.
45. Swathi, R. S.; Sebastian, K. L. *J. Chem. Phys.* 2008, 129, 054703.
46. Loh, K. P.; Bao, Q.; Eda, G.; Chhowalla, M. *Nat. Chem.* 2010, 2, 1015-1024.
47. Wang, Y.; Li, Z. H.; Hu, D. H.; Lin, C. T.; Li, J. H.; Lin, Y. H. *J. Am. Chem. Soc.* 2010, 132, 9274-9276.
48. Chou, S. S.; De, M.; Luo, J.; Rotello, V. M.; Huang, J.; Dravid, V. P. *J. Am. Chem. Soc.* 2012, 134, 16725-16733.
49. Lu, C. H.; Yang, H. H.; Zhu, C. L.; Chen, X.; Chen, G. N. *Angew. Chem. Int. Ed.* 2009, 48, 4785-4787.
50. Pei, H.; Li, J.; Lv, M.; Wang, J.; Gao, J.; Lu, J.; Li, Y.; Huang, Q.; Hu, J.; Fan, C. *J. Am. Chem. Soc.* 2012, 134, 13843-13849.
51. Wang, Y.; Li, Z.; Wang, J.; Li, J.; Lin, Y. *Trends Biotechnol.* 2011, 29, 205-212.
52. Allali-Hassani, A.; Pereira, M. P.; Navani, N. K.; Brown, E. D.; Li, Y. F. *Chem Bio Chem* 2007, 8, 2052-2057.

The invention claimed is:

1. A DNA aptamer that binds to *C. difficile* glutamate dehydrogenase, wherein said aptamer comprises a sequence selected from the group consisting of SEQ ID NOS: 16, 17, 19, 20, 21, 27 and 28 or a functional fragment of SEQ ID NOs: 16, 17, 19 or 20 which comprises SEQ ID NO:21 or modified aptamers thereof.

2. The aptamer of claim 1, wherein the aptamer comprises a sequence selected from the group consisting of SEQ ID NO:27 and 28.

3. The aptamer of claim 1, comprising the sequence of SEQ ID NO: 16 or 17.

4. An aptamer probe comprising the aptamer of claim 1 and a detectable label.

5. The aptamer probe of claim 4, wherein the detectable label is a fluorescent moiety.

6. The aptamer probe of claim 5, wherein the fluorescent moiety is a fluorophore.

7. The aptamer probe of claim 6, comprising the sequence of SEQ ID NO: 5.

8. A biosensor comprising:
a) an aptamer probe according to claim 4 adsorbed on
b) a nanomaterial;
wherein the aptamer changes conformation upon binding GDH and results in desorption from the nanomaterial.

9. The biosensor of claim 8, wherein the nanomaterial is reduced graphene oxide.

10. A biosensor comprising:
a) an aptamer probe according to claim 4 in association with
b) a quencher-oligonucleotide;
wherein the aptamer changes conformation upon binding GDH and results in release from the quencher-oligonucleotide.

11. A method for detecting the presence of *C. difficile* glutamate dehydrogenase in a test sample, comprising:
a) contacting said sample with the aptamer probe of claim 4, and
b) detecting a signal, wherein detection of a signal indicates the presence of *C. difficile* GDH in the test sample and lack of signal indicates that *C. difficile* GDH is not present.

12. A method for detecting the presence of *C. difficile* glutamate dehydrogenase in a test sample, comprising:
a) contacting said sample with the biosensor of claim 8, and b) detecting a signal, wherein detection of a signal indicates the presence of *C. difficile* GDH in the test sample and lack of signal indicates that *C. difficile* GDH is not present.

13. A method for detecting the presence of *C. difficile* glutamate dehydrogenase in a test sample, comprising:
   a) contacting said sample with the biosensor of claim 10, and
   b) detecting a signal, wherein detection of a signal indicates the presence of *C. difficile* GDH in the test sample and lack of signal indicates that *C. difficile* GDH is not present.

14. A method of detecting *C. difficile* infection in a subject comprising:
   a) testing a sample from the subject for the presence of *C. difficile* GDH by the method of claim 12; and
   b) if GDH is present, further comprising testing the sample for the presence of *C. difficile* toxins A and B; wherein the presence of GDH and the presence of toxins indicates that the subject has a *C. difficile* infection.

15. The method of claim 14, wherein testing for the presence of *C. difficile* toxins comprises a cell cytotoxicity neutralization assay, a toxin enzyme immunoassay or detection of toxin genes using PCR.

16. The method of claim 14, further comprising treating the subject for *C. difficile* infection if GDH and toxins are present.

17. A kit for detecting *C. difficile* glutamate dehydrogenase, wherein the kit comprises the biosensor of claim 10 and instructions for use of the kit.

18. The kit of claim 17, further comprising a blocking agent for non-specific binding to the nanomaterial.

19. The kit of claim 18, wherein the blocking agent is bovine serum albumin (BSA).

20. The kit of claim 19, wherein the BSA is at a concentration of 0.05 to 1%.

* * * * *

UNITED STATES PATENT AND TRADEMARK OFFICE
CERTIFICATE OF CORRECTION

PATENT NO. : 10,577,665 B2  
APPLICATION NO. : 16/121120  
DATED : March 3, 2020  
INVENTOR(S) : Li et al.

Page 1 of 1

It is certified that error appears in the above-identified patent and that said Letters Patent is hereby corrected as shown below:

In the Claims

Claim 1, Column 55, Line 50, cancel the term "20which" and insert the term -- 20 which --

Claim 15, Column 58, Line 4, cancel the term "*difficile*toxins" and insert the term -- *difficile* toxins --

Signed and Sealed this  
Twenty-third Day of March, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 31

<210> SEQ ID NO 1
<211> LENGTH: 82
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(61)
<223> OTHER INFORMATION: n is a, c, g, or t

<400> SEQUENCE: 1
caggtccatc gagtggtagg annnnnnnnn nnnnnnnnnn nnnnnnnnnn nnnnnnnnnn    60
ntcgcactgc tcctgaacgt ac                                             82

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
caggtccatc gagtggtagg a                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
gtacgttcag gagcagtgcg a                                              21

<210> SEQ ID NO 4
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: n = iSpC3

<400> SEQUENCE: 4
aaaaaaaaaa aangtacgtt caggagcagt gcga                                34

<210> SEQ ID NO 5
<211> LENGTH: 59
```

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: fam-labeled

<400> SEQUENCE: 5
taggaggagg tatttagtgc caagccatct caaacgacgt ctgagtcgca ctgctcctg    59

<210> SEQ ID NO 6
<211> LENGTH: 40
<212> TYPE: DNA
<213> ORGANISM: Artificial Sequence
<220> FEATURE:
<223> OTHER INFORMATION: Synthetic

<400> SEQUENCE: 6
ggaggtattt agtgccaagc catctcaaac gacgtctgag    40

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7
ccgagttccc aatattatgg ctatgcagga tacttcacct    40

<210> SEQ ID NO 8
<211> LENGTH: 40
<212> TYPE: DNA
<213> ORGANISM: Artificial Sequence
<220> FEATURE:
<223> OTHER INFORMATION: Synthetic

<400> SEQUENCE: 8
tgcagcggac agtgtgggac catcgctgcg gatgtatgaa    40

<210> SEQ ID NO 9
<211> LENGTH: 40
<212> TYPE: DNA
<213> ORGANISM: Artificial Sequence
<220> FEATURE:
<223> OTHER INFORMATION: Synthetic

<400> SEQUENCE: 9
tgagtactag ttccccagga gaaagcagat ccccaggtac    40

<210> SEQ ID NO 10
<211> LENGTH: 40
<212> TYPE: DNA
<213> ORGANISM: Artificial Sequence
<220> FEATURE:
<223> OTHER INFORMATION: Synthetic

<400> SEQUENCE: 10
gcacaggacg caagatgaat gcagcatacc agtccctaga    40

<210> SEQ ID NO 11
<211> LENGTH: 40
<212> TYPE: DNA
<213> ORGANISM: Artificial Sequence
<220> FEATURE:

<223> OTHER INFORMATION: Synthetic

<400> SEQUENCE: 11
cagctgtcga cgcgttaccg tgaacggaac accgatgacg                40

<210> SEQ ID NO 12
<211> LENGTH: 40
<212> TYPE: DNA
<213> ORGANISM: Artificial Sequence
<220> FEATURE:
<223> OTHER INFORMATION: Synthetic

<400> SEQUENCE: 12
cccaacccac gatgcgcaag aggaatgcag cctaccagca                40

<210> SEQ ID NO 13
<211> LENGTH: 40
<212> TYPE: DNA
<213> ORGANISM: Artificial Sequence
<220> FEATURE:
<223> OTHER INFORMATION: Synthetic

<400> SEQUENCE: 13
tgcgtgattg gaccagggaa agatgcaccg caagacaaga                40

<210> SEQ ID NO 14
<211> LENGTH: 40
<212> TYPE: DNA
<213> ORGANISM: Artificial Sequence
<220> FEATURE:
<223> OTHER INFORMATION: Synthetic

<400> SEQUENCE: 14
aggataatcc gatacgcaag aagaaagcag attaccagga                40

<210> SEQ ID NO 15
<211> LENGTH: 40
<212> TYPE: DNA
<213> ORGANISM: Artificial Sequence
<220> FEATURE:
<223> OTHER INFORMATION: Synthetic

<400> SEQUENCE: 15
caaagtcggc aaggtggaaa gcagccacac cacgactagt                40

<210> SEQ ID NO 16
<211> LENGTH: 82
<212> TYPE: DNA
<213> ORGANISM: Artificial Sequence
<220> FEATURE:
<223> OTHER INFORMATION: Synthetic

<400> SEQUENCE: 16
caggtccatc gagtggtagg aggaggtatt tagtgccaag ccatctcaaa cgacgtctga        60
gtcgcactgc tcctgaacgt ac                                                 82

<210> SEQ ID NO 17
<211> LENGTH: 59
<212> TYPE: DNA
<213> ORGANISM: Artificial Sequence
<220> FEATURE:
<223> OTHER INFORMATION: Synthetic

<400> SEQUENCE: 17
taggaggagg tatttagtgc caagccatct caaacgacgt ctgagtcgca ctgctcctg         59

<210> SEQ ID NO 18
<211> LENGTH: 43
<212> TYPE: DNA
<213> ORGANISM: Artificial Sequence
<220> FEATURE:
<223> OTHER INFORMATION: Synthetic

<400> SEQUENCE: 18
ggaggaggta tttagtgcca agccatctca aacgacgtct gag        43

<210> SEQ ID NO 19
<211> LENGTH: 52
<212> TYPE: DNA
<213> ORGANISM: Artificial Sequence
<220> FEATURE:
<223> OTHER INFORMATION: Synthetic

<400> SEQUENCE: 19
aggtatttag tgccaagcca tctcaaacga cgtctgagtc gcactgctcc tg        52

<210> SEQ ID NO 20
<211> LENGTH: 48
<212> TYPE: DNA
<213> ORGANISM: Artificial Sequence
<220> FEATURE:
<223> OTHER INFORMATION: Synthetic

<400> SEQUENCE: 20
aggtatttag tgccaagcca tctcaaacga cgtctgagtc gcactgct        48

<210> SEQ ID NO 21
<211> LENGTH: 45
<212> TYPE: DNA
<213> ORGANISM: Artificial Sequence
<220> FEATURE:
<223> OTHER INFORMATION: Synthetic

<400> SEQUENCE: 21
aggtatttag tgccaagcca tctcaaacga cgtctgagtc gcact        45

<210> SEQ ID NO 22
<211> LENGTH: 28
<212> TYPE: DNA
<213> ORGANISM: Artificial Sequence
<220> FEATURE:
<223> OTHER INFORMATION: Synthetic

<400> SEQUENCE: 22
agccatctca aacgacgtct gagtcgca        28

<210> SEQ ID NO 23
<211> LENGTH: 39
<212> TYPE: DNA
<213> ORGANISM: Artificial Sequence
<220> FEATURE:
<223> OTHER INFORMATION: Synthetic

<400> SEQUENCE: 23
tagtgccaag ccatctcaaa cgacgtctga gtcgcactg        39

<210> SEQ ID NO 24
<211> LENGTH: 37
<212> TYPE: DNA
<213> ORGANISM: Artificial Sequence
<220> FEATURE:

-continued

<223> OTHER INFORMATION: Synthetic

<400> SEQUENCE: 24
aggtatttag tgccaagcca tcgtcgcact gctcctg                             37

<210> SEQ ID NO 25
<211> LENGTH: 18
<212> TYPE: DNA
<213> ORGANISM: Artificial Sequence
<220> FEATURE:
<223> OTHER INFORMATION: Synthetic

<400> SEQUENCE: 25
caggtccatc gagtggta                                                 18

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
tcgcactgct cctgaacgta c                                             21

<210> SEQ ID NO 27
<211> LENGTH: 82
<212> TYPE: DNA
<213> ORGANISM: Artificial Sequence
<220> FEATURE:
<223> OTHER INFORMATION: Synthetic

<400> SEQUENCE: 27
caggtccatc gagtggtagg atgcagcgga cagtgtggga ccatcgctgc ggatgtatga   60
atcgcactgc tcctgaacgt ac                                            82

<210> SEQ ID NO 28
<211> LENGTH: 82
<212> TYPE: DNA
<213> ORGANISM: Artificial Sequence
<220> FEATURE:
<223> OTHER INFORMATION: Synthetic

<400> SEQUENCE: 28
caggtccatc gagtggtagg acccaaccca cgatgcgcaa gaggaatgca gcctaccagc   60
atcgcactgc tcctgaacgt ac                                            82

<210> SEQ ID NO 29
<211> LENGTH: 421
<212> TYPE: PRT
<213> ORGANISM: Clostridium difficile

<400> SEQUENCE: 29

Met Ser Gly Lys Asp Val Asn Val Phe Glu Met Ala Gln Ser Gln Val
1               5                   10                  15

Lys Asn Ala Cys Asp Lys Leu Gly Met Glu Pro Ala Val Tyr Glu Leu
            20                  25                  30

Leu Lys Glu Pro Met Arg Val Ile Glu Val Ser Ile Pro Val Lys Met
        35                  40                  45

Asp Asp Gly Ser Ile Lys Thr Phe Lys Gly Phe Arg Ser Gln His Asn
    50                  55                  60

Asp Ala Val Gly Pro Thr Lys Gly Gly Ile Arg Phe His Gln Asn Val

```
            65                  70                  75                  80
        Ser Arg Asp Glu Val Lys Ala Leu Ser Ile Trp Met Thr Phe Lys Cys
                        85                  90                  95

Ser Val Thr Gly Ile Pro Tyr Gly Gly Lys Gly Gly Ile Ile Val
                    100                 105                 110

Asp Pro Ser Thr Leu Ser Gln Gly Glu Leu Glu Arg Leu Ser Arg Gly
                        115                 120                 125

Tyr Ile Asp Gly Ile Tyr Lys Leu Ile Gly Glu Lys Val Asp Val Pro
                    130                 135                 140

Ala Pro Asp Val Asn Thr Asn Gly Gln Ile Met Ser Trp Met Val Asp
        145                 150                 155                 160

Glu Tyr Asn Lys Leu Thr Gly Gln Ser Ser Ile Gly Val Ile Thr Gly
                        165                 170                 175

Lys Pro Val Glu Phe Gly Gly Ser Leu Gly Arg Thr Ala Ala Thr Gly
                    180                 185                 190

Phe Gly Val Ala Val Thr Ala Arg Glu Ala Ala Lys Leu Gly Ile
                    195                 200                 205

Asp Met Lys Lys Ala Lys Ile Ala Val Gln Gly Ile Gly Asn Val Gly
                    210                 215                 220

Ser Tyr Thr Val Leu Asn Cys Glu Lys Leu Gly Gly Thr Val Val Ala
        225                 230                 235                 240

Met Ala Glu Trp Cys Lys Ser Glu Gly Ser Tyr Ala Ile Tyr Asn Glu
                        245                 250                 255

Asn Gly Leu Asp Gly Gln Ala Met Leu Asp Tyr Met Lys Glu His Gly
                    260                 265                 270

Asn Leu Leu Asn Phe Pro Gly Ala Lys Arg Ile Ser Leu Glu Glu Phe
                    275                 280                 285

Trp Ala Ser Asp Val Asp Ile Val Ile Pro Ala Ala Leu Glu Asn Ser
                    290                 295                 300

Ile Thr Lys Glu Val Ala Glu Ser Ile Lys Ala Lys Leu Val Cys Glu
        305                 310                 315                 320

Ala Ala Asn Gly Pro Thr Thr Pro Glu Ala Asp Glu Val Phe Ala Glu
                        325                 330                 335

Arg Gly Ile Val Leu Thr Pro Asp Ile Leu Thr Asn Ala Gly Gly Val
                    340                 345                 350

Thr Val Ser Tyr Phe Glu Trp Val Gln Asn Leu Tyr Gly Tyr Tyr Trp
                    355                 360                 365

Ser Glu Glu Glu Val Glu Gln Lys Gly Glu Ile Ala Met Val Lys Ala
                    370                 375                 380

Phe Glu Ser Ile Trp Lys Ile Lys Gly Glu Tyr Asn Val Thr Met Arg
        385                 390                 395                 400

Glu Ala Ala Tyr Met His Ser Ile Lys Lys Val Ala Glu Ala Met Lys
                        405                 410                 415

Leu Arg Gly Trp Tyr
                    420

<210> SEQ ID NO 30
<211> LENGTH: 2710
<212> TYPE: PRT
<213> ORGANISM: Clostridium difficile

<400> SEQUENCE: 30

Met Ser Leu Ile Ser Lys Glu Glu Leu Ile Lys Leu Ala Tyr Ser Ile
1               5                   10                  15
```

```
Arg Pro Arg Glu Asn Glu Tyr Lys Thr Ile Leu Thr Asn Leu Asp Glu
             20                  25                  30

Tyr Asn Lys Leu Thr Thr Asn Asn Glu Asn Lys Tyr Leu Gln Leu
         35                  40                  45

Lys Lys Leu Asn Glu Ser Ile Asp Val Phe Met Asn Lys Tyr Lys Thr
 50                  55                  60

Ser Ser Arg Asn Arg Ala Leu Ser Asn Leu Lys Lys Asp Ile Leu Lys
 65                  70                  75                  80

Glu Val Ile Leu Ile Lys Asn Ser Asn Thr Ser Pro Val Glu Lys Asn
                 85                  90                  95

Leu His Phe Val Trp Ile Gly Gly Glu Val Ser Asp Ile Ala Leu Glu
             100                 105                 110

Tyr Ile Lys Gln Trp Ala Asp Ile Asn Ala Glu Tyr Asn Ile Lys Leu
             115                 120                 125

Trp Tyr Asp Ser Glu Ala Phe Leu Val Asn Thr Leu Lys Lys Ala Ile
         130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                 165                 170                 175

Phe Ile Tyr Asp Arg Gln Lys Arg Phe Ile Asn Tyr Tyr Lys Ser Gln
             180                 185                 190

Ile Asn Lys Pro Thr Val Pro Thr Ile Asp Asp Ile Ile Lys Ser His
         195                 200                 205

Leu Val Ser Glu Tyr Asn Arg Asp Glu Thr Val Leu Glu Ser Tyr Arg
210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
             245                 250                 255

Glu Leu Leu Asn Arg Gly Asn Leu Ala Ala Ala Ser Asp Ile Val Arg
         260                 265                 270

Leu Leu Ala Leu Lys Asn Phe Gly Gly Val Tyr Leu Asp Val Asp Met
     275                 280                 285

Leu Pro Gly Ile His Ser Asp Leu Phe Lys Thr Ile Ser Arg Pro Ser
 290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
             325                 330                 335

Leu Asp Gln Gln Leu Lys Asp Asn Phe Lys Leu Ile Ile Glu Ser Lys
         340                 345                 350

Ser Glu Lys Ser Glu Ile Phe Ser Lys Leu Glu Asn Leu Asn Val Ser
     355                 360                 365

Asp Leu Glu Ile Lys Ile Ala Phe Ala Leu Gly Ser Val Ile Asn Gln
 370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
             405                 410                 415

Ile Glu Ser Asp Asn Asn Phe Thr Asp Thr Thr Lys Ile Phe His Asp
         420                 425                 430

Ser Leu Phe Asn Ser Ala Thr Ala Glu Asn Ser Met Phe Leu Thr Lys
```

```
            435                 440                 445
Ile Ala Pro Tyr Leu Gln Val Gly Phe Met Pro Glu Ala Arg Ser Thr
450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                    485                 490                 495

Leu Ile Glu Phe Lys Phe Pro Glu Asn Asn Leu Ser Gln Leu Thr Glu
                500                 505                 510

Gln Glu Ile Asn Ser Leu Trp Ser Phe Asp Gln Ala Ser Ala Lys Tyr
                515                 520                 525

Gln Phe Glu Lys Tyr Val Arg Asp Tyr Thr Gly Gly Ser Leu Ser Glu
530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Glu Ala Gly Ser
                    565                 570                 575

Lys Asn Tyr Val His Tyr Ile Ile Gln Leu Gln Gly Asp Asp Ile Ser
                580                 585                 590

Tyr Glu Ala Thr Cys Asn Leu Phe Ser Lys Asn Pro Lys Asn Ser Ile
                595                 600                 605

Ile Ile Gln Arg Asn Met Asn Glu Ser Ala Lys Ser Tyr Phe Leu Ser
610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                    645                 650                 655

Lys Asp Glu Phe Asn Thr Ser Glu Phe Ala Arg Leu Ser Val Asp Ser
                660                 665                 670

Leu Ser Asn Glu Ile Ser Ser Phe Leu Asp Thr Ile Lys Leu Asp Ile
                675                 680                 685

Ser Pro Lys Asn Val Glu Val Asn Leu Leu Gly Cys Asn Met Phe Ser
690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
                740                 745                 750

Arg Lys Glu Leu Leu Ala His Ser Gly Lys Trp Ile Asn Lys Glu Glu
                755                 760                 765

Ala Ile Met Ser Asp Leu Ser Ser Lys Glu Tyr Ile Phe Phe Asp Ser
                770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
                820                 825                 830

Ser Ile Gly Asp Tyr Ile Tyr Tyr Glu Lys Leu Glu Pro Val Lys Asn
                835                 840                 845

Ile Ile His Asn Ser Ile Asp Asp Leu Ile Asp Glu Phe Asn Leu Leu
                850                 855                 860
```

-continued

```
Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
            885                 890                 895

Thr Tyr Ser Val Arg Phe Ile Asn Lys Ser Asn Gly Glu Ser Val Tyr
        900                 905                 910

Val Glu Thr Glu Lys Glu Ile Phe Ser Lys Tyr Ser Glu His Ile Thr
    915                 920                 925

Lys Glu Ile Ser Thr Ile Lys Asn Ser Ile Ile Thr Asp Val Asn Gly
930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu Asn Thr Ile Tyr Asp Ser Ile Gln
        995                 1000                1005

Leu Val Asn Leu Ile Ser Asn Ala Val Asn Asp Thr Ile Asn Val
    1010                1015                1020

Leu Pro Thr Ile Thr Glu Gly Ile Pro Ile Val Ser Thr Ile Leu
    1025                1030                1035

Asp Gly Ile Asn Leu Gly Ala Ala Ile Lys Glu Leu Leu Asp Glu
    1040                1045                1050

His Asp Pro Leu Leu Lys Lys Glu Leu Glu Ala Lys Val Gly Val
    1055                1060                1065

Leu Ala Ile Asn Met Ser Leu Ser Ile Ala Ala Thr Val Ala Ser
    1070                1075                1080

Ile Val Gly Ile Gly Ala Glu Val Thr Ile Phe Leu Leu Pro Ile
    1085                1090                1095

Ala Gly Ile Ser Ala Gly Ile Pro Ser Leu Val Asn Asn Glu Leu
    1100                1105                1110

Ile Leu His Asp Lys Ala Thr Ser Val Val Asn Tyr Phe Asn His
    1115                1120                1125

Leu Ser Glu Ser Lys Lys Tyr Gly Pro Leu Lys Thr Glu Asp Asp
    1130                1135                1140

Lys Ile Leu Val Pro Ile Asp Asp Leu Val Ile Ser Glu Ile Asp
    1145                1150                1155

Phe Asn Asn Asn Ser Ile Lys Leu Gly Thr Cys Asn Ile Leu Ala
    1160                1165                1170

Met Glu Gly Gly Ser Gly His Thr Val Thr Gly Asn Ile Asp His
    1175                1180                1185

Phe Phe Ser Ser Pro Ser Ile Ser Ser His Ile Pro Ser Leu Ser
    1190                1195                1200

Ile Tyr Ser Ala Ile Gly Ile Glu Thr Glu Asn Leu Asp Phe Ser
    1205                1210                1215

Lys Lys Ile Met Met Leu Pro Asn Ala Pro Ser Arg Val Phe Trp
    1220                1225                1230

Trp Glu Thr Gly Ala Val Pro Gly Leu Arg Ser Leu Glu Asn Asp
    1235                1240                1245

Gly Thr Arg Leu Leu Asp Ser Ile Arg Asp Leu Tyr Pro Gly Lys
    1250                1255                1260
```

Phe Tyr Trp Arg Phe Tyr Ala Phe Phe Asp Tyr Ala Ile Thr Thr
1265                1270                1275

Leu Lys Pro Val Tyr Glu Asp Thr Asn Ile Lys Ile Lys Leu Asp
1280                1285                1290

Lys Asp Thr Arg Asn Phe Ile Met Pro Thr Ile Thr Thr Asn Glu
1295                1300                1305

Ile Arg Asn Lys Leu Ser Tyr Ser Phe Asp Gly Ala Gly Gly Thr
1310                1315                1320

Tyr Ser Leu Leu Leu Ser Ser Tyr Pro Ile Ser Thr Asn Ile Asn
1325                1330                1335

Leu Ser Lys Asp Asp Leu Trp Ile Phe Asn Ile Asp Asn Glu Val
1340                1345                1350

Arg Glu Ile Ser Ile Glu Asn Gly Thr Ile Lys Lys Gly Lys Leu
1355                1360                1365

Ile Lys Asp Val Leu Ser Lys Ile Asp Ile Asn Lys Asn Lys Leu
1370                1375                1380

Ile Ile Gly Asn Gln Thr Ile Asp Phe Ser Gly Asp Ile Asp Asn
1385                1390                1395

Lys Asp Arg Tyr Ile Phe Leu Thr Cys Glu Leu Asp Asp Lys Ile
1400                1405                1410

Ser Leu Ile Ile Glu Ile Asn Leu Val Ala Lys Ser Tyr Ser Leu
1415                1420                1425

Leu Leu Ser Gly Asp Lys Asn Tyr Leu Ile Ser Asn Leu Ser Asn
1430                1435                1440

Thr Ile Glu Lys Ile Asn Thr Leu Gly Leu Asp Ser Lys Asn Ile
1445                1450                1455

Ala Tyr Asn Tyr Thr Asp Glu Ser Asn Asn Lys Tyr Phe Gly Ala
1460                1465                1470

Ile Ser Lys Thr Ser Gln Lys Ser Ile Ile His Tyr Lys Lys Asp
1475                1480                1485

Ser Lys Asn Ile Leu Glu Phe Tyr Asn Asp Ser Thr Leu Glu Phe
1490                1495                1500

Asn Ser Lys Asp Phe Ile Ala Glu Asp Ile Asn Val Phe Met Lys
1505                1510                1515

Asp Asp Ile Asn Thr Ile Thr Gly Lys Tyr Tyr Val Asp Asn Asn
1520                1525                1530

Thr Asp Lys Ser Ile Asp Phe Ser Ile Ser Leu Val Ser Lys Asn
1535                1540                1545

Gln Val Lys Val Asn Gly Leu Tyr Leu Asn Glu Ser Val Tyr Ser
1550                1555                1560

Ser Tyr Leu Asp Phe Val Lys Asn Ser Asp Gly His His Asn Thr
1565                1570                1575

Ser Asn Phe Met Asn Leu Phe Leu Asp Asn Ile Ser Phe Trp Lys
1580                1585                1590

Leu Phe Gly Phe Glu Asn Ile Asn Phe Val Ile Asp Lys Tyr Phe
1595                1600                1605

Thr Leu Val Gly Lys Thr Asn Leu Gly Tyr Val Glu Phe Ile Cys
1610                1615                1620

Asp Asn Asn Lys Asn Ile Asp Ile Tyr Phe Gly Glu Trp Lys Thr
1625                1630                1635

Ser Ser Ser Lys Ser Thr Ile Phe Ser Gly Asn Gly Arg Asn Val
1640                1645                1650

Val Val Glu Pro Ile Tyr Asn Pro Asp Thr Gly Glu Asp Ile Ser

-continued

```
            1655                1660                1665

Thr Ser Leu Asp Phe Ser Tyr Glu Pro Leu Tyr Gly Ile Asp Arg
    1670                1675                1680

Tyr Ile Asn Lys Val Leu Ile Ala Pro Asp Leu Tyr Thr Ser Leu
    1685                1690                1695

Ile Asn Ile Asn Thr Asn Tyr Tyr Ser Asn Glu Tyr Tyr Pro Glu
    1700                1705                1710

Ile Ile Val Leu Asn Pro Asn Thr Phe His Lys Lys Val Asn Ile
    1715                1720                1725

Asn Leu Asp Ser Ser Phe Glu Tyr Lys Trp Ser Thr Glu Gly
    1730                1735                1740

Ser Asp Phe Ile Leu Val Arg Tyr Leu Glu Glu Ser Asn Lys Lys
    1745                1750                1755

Ile Leu Gln Lys Ile Arg Ile Lys Gly Ile Leu Ser Asn Thr Gln
    1760                1765                1770

Ser Phe Asn Lys Met Ser Ile Asp Phe Lys Asp Ile Lys Lys Leu
    1775                1780                1785

Ser Leu Gly Tyr Ile Met Ser Asn Phe Lys Ser Phe Asn Ser Glu
    1790                1795                1800

Asn Glu Leu Asp Arg Asp His Leu Gly Phe Lys Ile Ile Asp Asn
    1805                1810                1815

Lys Thr Tyr Tyr Tyr Asp Glu Asp Ser Lys Leu Val Lys Gly Leu
    1820                1825                1830

Ile Asn Ile Asn Asn Ser Leu Phe Tyr Phe Asp Pro Ile Glu Phe
    1835                1840                1845

Asn Leu Val Thr Gly Trp Gln Thr Ile Asn Gly Lys Lys Tyr Tyr
    1850                1855                1860

Phe Asp Ile Asn Thr Gly Ala Ala Leu Thr Ser Tyr Lys Ile Ile
    1865                1870                1875

Asn Gly Lys His Phe Tyr Phe Asn Asn Asp Gly Val Met Gln Leu
    1880                1885                1890

Gly Val Phe Lys Gly Pro Asp Gly Phe Glu Tyr Phe Ala Pro Ala
    1895                1900                1905

Asn Thr Gln Asn Asn Asn Ile Glu Gly Gln Ala Ile Val Tyr Gln
    1910                1915                1920

Ser Lys Phe Leu Thr Leu Asn Gly Lys Lys Tyr Tyr Phe Asp Asn
    1925                1930                1935

Asn Ser Lys Ala Val Thr Gly Trp Arg Ile Ile Asn Asn Glu Lys
    1940                1945                1950

Tyr Tyr Phe Asn Pro Asn Asn Ala Ile Ala Ala Val Gly Leu Gln
    1955                1960                1965

Val Ile Asp Asn Asn Lys Tyr Tyr Phe Asn Pro Asp Thr Ala Ile
    1970                1975                1980

Ile Ser Lys Gly Trp Gln Thr Val Asn Gly Ser Arg Tyr Tyr Phe
    1985                1990                1995

Asp Thr Asp Thr Ala Ile Ala Phe Asn Gly Tyr Lys Thr Ile Asp
    2000                2005                2010

Gly Lys His Phe Tyr Phe Asp Ser Asp Cys Val Val Lys Ile Gly
    2015                2020                2025

Val Phe Ser Thr Ser Asn Gly Phe Glu Tyr Phe Ala Pro Ala Asn
    2030                2035                2040

Thr Tyr Asn Asn Asn Ile Glu Gly Gln Ala Ile Val Tyr Gln Ser
    2045                2050                2055
```

-continued

Lys Phe Leu Thr Leu Asn Gly Lys Lys Tyr Tyr Phe Asp Asn Asn
2060                2065            2070

Ser Lys Ala Val Thr Gly Leu Gln Thr Ile Asp Ser Lys Lys Tyr
2075                2080            2085

Tyr Phe Asn Thr Asn Thr Ala Glu Ala Ala Thr Gly Trp Gln Thr
2090                2095            2100

Ile Asp Gly Lys Lys Tyr Tyr Phe Asn Thr Asn Thr Ala Glu Ala
2105                2110            2115

Ala Thr Gly Trp Gln Thr Ile Asp Gly Lys Lys Tyr Tyr Phe Asn
2120                2125            2130

Thr Asn Thr Ala Ile Ala Ser Thr Gly Tyr Thr Ile Ile Asn Gly
2135                2140            2145

Lys His Phe Tyr Phe Asn Thr Asp Gly Ile Met Gln Ile Gly Val
2150                2155            2160

Phe Lys Gly Pro Asn Gly Phe Glu Tyr Phe Ala Pro Ala Asn Thr
2165                2170            2175

Asp Ala Asn Asn Ile Glu Gly Gln Ala Ile Leu Tyr Gln Asn Glu
2180                2185            2190

Phe Leu Thr Leu Asn Gly Lys Lys Tyr Tyr Phe Gly Ser Asp Ser
2195                2200            2205

Lys Ala Val Thr Gly Trp Arg Ile Ile Asn Asn Lys Lys Tyr Tyr
2210                2215            2220

Phe Asn Pro Asn Asn Ala Ile Ala Ala Ile His Leu Cys Thr Ile
2225                2230            2235

Asn Asn Asp Lys Tyr Tyr Phe Ser Tyr Asp Gly Ile Leu Gln Asn
2240                2245            2250

Gly Tyr Ile Thr Ile Glu Arg Asn Asn Phe Tyr Phe Asp Ala Asn
2255                2260            2265

Asn Glu Ser Lys Met Val Thr Gly Val Phe Lys Gly Pro Asn Gly
2270                2275            2280

Phe Glu Tyr Phe Ala Pro Ala Asn Thr His Asn Asn Asn Ile Glu
2285                2290            2295

Gly Gln Ala Ile Val Tyr Gln Asn Lys Phe Leu Thr Leu Asn Gly
2300                2305            2310

Lys Lys Tyr Tyr Phe Asp Asn Asp Ser Lys Ala Val Thr Gly Trp
2315                2320            2325

Gln Thr Ile Asp Gly Lys Lys Tyr Tyr Phe Asn Leu Asn Thr Ala
2330                2335            2340

Glu Ala Ala Thr Gly Trp Gln Thr Ile Asp Gly Lys Lys Tyr Tyr
2345                2350            2355

Phe Asn Leu Asn Thr Ala Glu Ala Ala Thr Gly Trp Gln Thr Ile
2360                2365            2370

Asp Gly Lys Lys Tyr Tyr Phe Asn Thr Asn Thr Phe Ile Ala Ser
2375                2380            2385

Thr Gly Tyr Thr Ser Ile Asn Gly Lys His Phe Tyr Phe Asn Thr
2390                2395            2400

Asp Gly Ile Met Gln Ile Gly Val Phe Lys Gly Pro Asn Gly Phe
2405                2410            2415

Glu Tyr Phe Ala Pro Ala Asn Thr Asp Ala Asn Asn Ile Glu Gly
2420                2425            2430

Gln Ala Ile Leu Tyr Gln Asn Lys Phe Leu Thr Leu Asn Gly Lys
2435                2440            2445

```
Lys Tyr Tyr Phe Gly Ser Asp Ser Lys Ala Val Thr Gly Leu Arg
     2450                2455                2460

Thr Ile Asp Gly Lys Lys Tyr Tyr Phe Asn Thr Asn Thr Ala Val
    2465                2470                2475

Ala Val Thr Gly Trp Gln Thr Ile Asn Gly Lys Lys Tyr Tyr Phe
    2480                2485                2490

Asn Thr Asn Thr Ser Ile Ala Ser Thr Gly Tyr Thr Ile Ile Ser
    2495                2500                2505

Gly Lys His Phe Tyr Phe Asn Thr Asp Gly Ile Met Gln Ile Gly
    2510                2515                2520

Val Phe Lys Gly Pro Asp Gly Phe Glu Tyr Phe Ala Pro Ala Asn
    2525                2530                2535

Thr Asp Ala Asn Asn Ile Glu Gly Gln Ala Ile Arg Tyr Gln Asn
    2540                2545                2550

Arg Phe Leu Tyr Leu His Asp Asn Ile Tyr Tyr Phe Gly Asn Asn
    2555                2560                2565

Ser Lys Ala Ala Thr Gly Trp Val Thr Ile Asp Gly Asn Arg Tyr
    2570                2575                2580

Tyr Phe Glu Pro Asn Thr Ala Met Gly Ala Asn Gly Tyr Lys Thr
    2585                2590                2595

Ile Asp Asn Lys Asn Phe Tyr Phe Arg Asn Gly Leu Pro Gln Ile
    2600                2605                2610

Gly Val Phe Lys Gly Ser Asn Gly Phe Glu Tyr Phe Ala Pro Ala
    2615                2620                2625

Asn Thr Asp Ala Asn Asn Ile Glu Gly Gln Ala Ile Arg Tyr Gln
    2630                2635                2640

Asn Arg Phe Leu His Leu Leu Gly Lys Ile Tyr Tyr Phe Gly Asn
    2645                2650                2655

Asn Ser Lys Ala Val Thr Gly Trp Gln Thr Ile Asn Gly Lys Val
    2660                2665                2670

Tyr Tyr Phe Met Pro Asp Thr Ala Met Ala Ala Ala Gly Gly Leu
    2675                2680                2685

Phe Glu Ile Asp Gly Val Ile Tyr Phe Phe Gly Val Asp Gly Val
    2690                2695                2700

Lys Ala Pro Gly Ile Tyr Gly
    2705                2710

<210> SEQ ID NO 31
<211> LENGTH: 2366
<212> TYPE: PRT
<213> ORGANISM: Clostridium difficile

<400> SEQUENCE: 31

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95
```

```
Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
            115                 120                 125

Val Phe Tyr Asp Ser Asn Ala Phe Leu Ile Asn Thr Leu Lys Lys Thr
130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
            195                 200                 205

Tyr Leu Ser Asn Glu Tyr Ser Lys Glu Ile Asp Glu Leu Asn Thr Tyr
210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
            275                 280                 285

Met Leu Pro Gly Ile Gln Pro Asp Leu Phe Glu Ser Ile Glu Lys Pro
            290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
            355                 360                 365

Ser Pro Leu Glu Val Lys Ile Ala Phe Asn Ser Lys Gly Ile Ile Asn
370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
            435                 440                 445

Glu Leu Gly Lys Tyr Leu Arg Val Gly Phe Phe Pro Asp Val Lys Thr
            450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510
```

Glu Gln Glu Met Ala Ser Leu Trp Ser Phe Asp Asp Ala Arg Ala Lys
            515                 520                 525
Ala Gln Phe Glu Glu Tyr Lys Arg Asn Tyr Phe Glu Gly Ser Leu Gly
    530                 535                 540
Glu Asp Asp Asn Leu Asp Phe Ser Gln Asn Ile Val Val Asp Lys Glu
545                 550                 555                 560
Tyr Leu Leu Glu Lys Ile Ser Ser Leu Ala Arg Ser Ser Glu Arg Gly
                565                 570                 575
Tyr Ile His Tyr Ile Val Gln Leu Gln Gly Asp Lys Ile Ser Tyr Glu
            580                 585                 590
Ala Ala Cys Asn Leu Phe Ala Lys Thr Pro Tyr Asp Ser Val Leu Phe
        595                 600                 605
Gln Lys Asn Ile Glu Asp Ser Glu Ile Ala Tyr Tyr Tyr Asn Pro Gly
    610                 615                 620
Asp Gly Glu Ile Gln Glu Ile Asp Lys Tyr Lys Ile Pro Ser Ile Ile
625                 630                 635                 640
Ser Asp Arg Pro Lys Ile Lys Leu Thr Phe Ile Gly His Gly Lys Asp
                645                 650                 655
Glu Phe Asn Thr Asp Ile Phe Ala Gly Phe Asp Val Asp Ser Leu Ser
            660                 665                 670
Thr Glu Ile Glu Ala Ala Ile Asp Leu Ala Lys Glu Asp Ile Ser Pro
        675                 680                 685
Lys Ser Ile Glu Ile Asn Leu Leu Gly Cys Asn Met Phe Ser Tyr Ser
    690                 695                 700
Ile Asn Val Glu Glu Thr Tyr Pro Gly Lys Leu Leu Leu Lys Val Lys
705                 710                 715                 720
Asp Lys Ile Ser Glu Leu Met Pro Ser Ile Ser Gln Asp Ser Ile Ile
                725                 730                 735
Val Ser Ala Asn Gln Tyr Glu Val Arg Ile Asn Ser Glu Gly Arg Arg
            740                 745                 750
Glu Leu Leu Asp His Ser Gly Glu Trp Ile Asn Lys Glu Glu Ser Ile
        755                 760                 765
Ile Lys Asp Ile Ser Ser Lys Glu Tyr Ile Ser Phe Asn Pro Lys Glu
    770                 775                 780
Asn Lys Ile Thr Val Lys Ser Lys Asn Leu Pro Glu Leu Ser Thr Leu
785                 790                 795                 800
Leu Gln Glu Ile Arg Asn Asn Ser Asn Ser Ser Asp Ile Glu Leu Glu
                805                 810                 815
Glu Lys Val Met Leu Thr Glu Cys Glu Ile Asn Val Ile Ser Asn Ile
            820                 825                 830
Asp Thr Gln Ile Val Glu Glu Arg Ile Glu Glu Ala Lys Asn Leu Thr
        835                 840                 845
Ser Asp Ser Ile Asn Tyr Ile Lys Asp Glu Phe Lys Leu Ile Glu Ser
    850                 855                 860
Ile Ser Asp Ala Leu Cys Asp Leu Lys Gln Gln Asn Glu Leu Glu Asp
865                 870                 875                 880
Ser His Phe Ile Ser Phe Glu Asp Ile Ser Glu Thr Asp Glu Gly Phe
                885                 890                 895
Ser Ile Arg Phe Ile Asn Lys Glu Thr Gly Glu Ser Ile Phe Val Glu
            900                 905                 910
Thr Glu Lys Thr Ile Phe Ser Glu Tyr Ala Asn His Ile Thr Glu Glu
        915                 920                 925
Ile Ser Lys Ile Lys Gly Thr Ile Phe Asp Thr Val Asn Gly Lys Leu

-continued

```
                930             935             940
Val Lys Lys Val Asn Leu Asp Thr Thr His Glu Val Asn Thr Leu Asn
945                 950             955                 960

Ala Ala Phe Phe Ile Gln Ser Leu Ile Glu Tyr Asn Ser Ser Lys Glu
            965             970             975

Ser Leu Ser Asn Leu Ser Val Ala Met Lys Val Gln Val Tyr Ala Gln
            980             985             990

Leu Phe Ser Thr Gly Leu Asn Thr Ile Thr Asp Ala Ala Lys Val Val
            995             1000            1005

Glu Leu Val Ser Thr Ala Leu Asp Glu Thr Ile Asp Leu Leu Pro
    1010            1015            1020

Thr Leu Ser Glu Gly Leu Pro Ile Ile Ala Thr Ile Ile Asp Gly
    1025            1030            1035

Val Ser Leu Gly Ala Ala Ile Lys Glu Leu Ser Glu Thr Ser Asp
    1040            1045            1050

Pro Leu Leu Arg Gln Glu Ile Glu Ala Lys Ile Gly Ile Met Ala
    1055            1060            1065

Val Asn Leu Thr Thr Ala Thr Thr Ala Ile Ile Thr Ser Ser Leu
    1070            1075            1080

Gly Ile Ala Ser Gly Phe Ser Ile Leu Leu Val Pro Leu Ala Gly
    1085            1090            1095

Ile Ser Ala Gly Ile Pro Ser Leu Val Asn Asn Glu Leu Val Leu
    1100            1105            1110

Arg Asp Lys Ala Thr Lys Val Val Asp Tyr Phe Lys His Val Ser
    1115            1120            1125

Leu Val Glu Thr Glu Gly Val Phe Thr Leu Leu Asp Asp Lys Ile
    1130            1135            1140

Met Met Pro Gln Asp Asp Leu Val Ile Ser Glu Ile Asp Phe Asn
    1145            1150            1155

Asn Asn Ser Ile Val Leu Gly Lys Cys Glu Ile Trp Arg Met Glu
    1160            1165            1170

Gly Gly Ser Gly His Thr Val Thr Asp Asp Ile Asp His Phe Phe
    1175            1180            1185

Ser Ala Pro Ser Ile Thr Tyr Arg Glu Pro His Leu Ser Ile Tyr
    1190            1195            1200

Asp Val Leu Glu Val Gln Lys Glu Glu Leu Asp Leu Ser Lys Asp
    1205            1210            1215

Leu Met Val Leu Pro Asn Ala Pro Asn Arg Val Phe Ala Trp Glu
    1220            1225            1230

Thr Gly Trp Thr Pro Gly Leu Arg Ser Leu Glu Asn Asp Gly Thr
    1235            1240            1245

Lys Leu Leu Asp Arg Ile Arg Asp Asn Tyr Glu Gly Glu Phe Tyr
    1250            1255            1260

Trp Arg Tyr Phe Ala Phe Ile Ala Asp Ala Leu Ile Thr Thr Leu
    1265            1270            1275

Lys Pro Arg Tyr Glu Asp Thr Asn Ile Arg Ile Asn Leu Asp Ser
    1280            1285            1290

Asn Thr Arg Ser Phe Ile Val Pro Ile Ile Thr Thr Glu Tyr Ile
    1295            1300            1305

Arg Glu Lys Leu Ser Tyr Ser Phe Tyr Gly Ser Gly Gly Thr Tyr
    1310            1315            1320

Ala Leu Ser Leu Ser Gln Tyr Asn Met Gly Ile Asn Ile Glu Leu
    1325            1330            1335
```

-continued

Ser Glu Ser Asp Val Trp Ile Ile Asp Val Asp Asn Val Val Arg
1340                1345                1350

Asp Val Thr Ile Glu Ser Asp Lys Ile Lys Lys Gly Asp Leu Ile
    1355                1360                1365

Glu Gly Ile Leu Ser Thr Leu Ser Ile Glu Glu Asn Lys Ile Ile
1370                1375                1380

Leu Asn Ser His Glu Ile Asn Phe Ser Gly Glu Val Asn Gly Ser
1385                1390                1395

Asn Gly Phe Val Ser Leu Thr Phe Ser Ile Leu Glu Gly Ile Asn
1400                1405                1410

Ala Ile Ile Glu Val Asp Leu Leu Ser Lys Ser Tyr Lys Leu Leu
1415                1420                1425

Ile Ser Gly Glu Leu Lys Ile Leu Met Leu Asn Ser Asn His Ile
1430                1435                1440

Gln Gln Lys Ile Asp Tyr Ile Gly Phe Asn Ser Glu Leu Gln Lys
1445                1450                1455

Asn Ile Pro Tyr Ser Phe Val Asp Ser Glu Gly Lys Glu Asn Gly
1460                1465                1470

Phe Ile Asn Gly Ser Thr Lys Glu Gly Leu Phe Val Ser Glu Leu
1475                1480                1485

Pro Asp Val Val Leu Ile Ser Lys Val Tyr Met Asp Asp Ser Lys
1490                1495                1500

Pro Ser Phe Gly Tyr Tyr Ser Asn Asn Leu Lys Asp Val Lys Val
1505                1510                1515

Ile Thr Lys Asp Asn Val Asn Ile Leu Thr Gly Tyr Tyr Leu Lys
1520                1525                1530

Asp Asp Ile Lys Ile Ser Leu Ser Leu Thr Leu Gln Asp Glu Lys
1535                1540                1545

Thr Ile Lys Leu Asn Ser Val His Leu Asp Glu Ser Gly Val Ala
1550                1555                1560

Glu Ile Leu Lys Phe Met Asn Arg Lys Gly Asn Thr Asn Thr Ser
1565                1570                1575

Asp Ser Leu Met Ser Phe Leu Glu Ser Met Asn Ile Lys Ser Ile
1580                1585                1590

Phe Val Asn Phe Leu Gln Ser Asn Ile Lys Phe Ile Leu Asp Ala
1595                1600                1605

Asn Phe Ile Ile Ser Gly Thr Thr Ser Ile Gly Gln Phe Glu Phe
1610                1615                1620

Ile Cys Asp Glu Asn Asp Asn Ile Gln Pro Tyr Phe Ile Lys Phe
1625                1630                1635

Asn Thr Leu Glu Thr Asn Tyr Thr Leu Tyr Val Gly Asn Arg Gln
1640                1645                1650

Asn Met Ile Val Glu Pro Asn Tyr Asp Leu Asp Asp Ser Gly Asp
1655                1660                1665

Ile Ser Ser Thr Val Ile Asn Phe Ser Gln Lys Tyr Leu Tyr Gly
1670                1675                1680

Ile Asp Ser Cys Val Asn Lys Val Val Ile Ser Pro Asn Ile Tyr
1685                1690                1695

Thr Asp Glu Ile Asn Ile Thr Pro Val Tyr Glu Thr Asn Asn Thr
1700                1705                1710

Tyr Pro Glu Val Ile Val Leu Asp Ala Asn Tyr Ile Asn Glu Lys
1715                1720                1725

```
Ile Asn Val Asn Ile Asn Asp Leu Ser Ile Arg Tyr Val Trp Ser
1730                1735                1740

Asn Asp Gly Asn Asp Phe Ile Leu Met Ser Thr Ser Glu Glu Asn
    1745                1750                1755

Lys Val Ser Gln Val Lys Ile Arg Phe Val Asn Val Phe Lys Asp
    1760                1765                1770

Lys Thr Leu Ala Asn Lys Leu Ser Phe Asn Phe Ser Asp Lys Gln
    1775                1780                1785

Asp Val Pro Val Ser Glu Ile Ile Leu Ser Phe Thr Pro Ser Tyr
    1790                1795                1800

Tyr Glu Asp Gly Leu Ile Gly Tyr Asp Leu Gly Leu Val Ser Leu
    1805                1810                1815

Tyr Asn Glu Lys Phe Tyr Ile Asn Asn Phe Gly Met Met Val Ser
    1820                1825                1830

Gly Leu Ile Tyr Ile Asn Asp Ser Leu Tyr Tyr Phe Lys Pro Pro
    1835                1840                1845

Val Asn Asn Leu Ile Thr Gly Phe Val Thr Val Gly Asp Asp Lys
    1850                1855                1860

Tyr Tyr Phe Asn Pro Ile Asn Gly Gly Ala Ala Ser Ile Gly Glu
    1865                1870                1875

Thr Ile Ile Asp Asp Lys Asn Tyr Tyr Phe Asn Gln Ser Gly Val
    1880                1885                1890

Leu Gln Thr Gly Val Phe Ser Thr Glu Asp Gly Phe Lys Tyr Phe
    1895                1900                1905

Ala Pro Ala Asn Thr Leu Asp Glu Asn Leu Glu Gly Glu Ala Ile
    1910                1915                1920

Asp Phe Thr Gly Lys Leu Ile Ile Asp Glu Asn Ile Tyr Tyr Phe
    1925                1930                1935

Asp Asp Asn Tyr Arg Gly Ala Val Glu Trp Lys Glu Leu Asp Gly
    1940                1945                1950

Glu Met His Tyr Phe Ser Pro Glu Thr Gly Lys Ala Phe Lys Gly
    1955                1960                1965

Leu Asn Gln Ile Gly Asp Tyr Lys Tyr Tyr Phe Asn Ser Asp Gly
    1970                1975                1980

Val Met Gln Lys Gly Phe Val Ser Ile Asn Asp Asn Lys His Tyr
    1985                1990                1995

Phe Asp Asp Ser Gly Val Met Lys Val Gly Tyr Thr Glu Ile Asp
    2000                2005                2010

Gly Lys His Phe Tyr Phe Ala Glu Asn Gly Glu Met Gln Ile Gly
    2015                2020                2025

Val Phe Asn Thr Glu Asp Gly Phe Lys Tyr Phe Ala His His Asn
    2030                2035                2040

Glu Asp Leu Gly Asn Glu Glu Gly Glu Glu Ile Ser Tyr Ser Gly
    2045                2050                2055

Ile Leu Asn Phe Asn Asn Lys Ile Tyr Tyr Phe Asp Asp Ser Phe
    2060                2065                2070

Thr Ala Val Val Gly Trp Lys Asp Leu Glu Asp Gly Ser Lys Tyr
    2075                2080                2085

Tyr Phe Asp Glu Asp Thr Ala Glu Ala Tyr Ile Gly Leu Ser Leu
    2090                2095                2100

Ile Asn Asp Gly Gln Tyr Tyr Phe Asn Asp Asp Gly Ile Met Gln
    2105                2110                2115

Val Gly Phe Val Thr Ile Asn Asp Lys Val Phe Tyr Phe Ser Asp
```

-continued

```
                2120                    2125                    2130
Ser Gly Ile Ile Glu Ser Gly Val Gln Asn Ile Asp Asp Asn Tyr
                2135                    2140                    2145

Phe Tyr Ile Asp Asp Asn Gly Ile Val Gln Ile Gly Val Phe Asp
                2150                    2155                    2160

Thr Ser Asp Gly Tyr Lys Tyr Phe Ala Pro Ala Asn Thr Val Asn
                2165                    2170                    2175

Asp Asn Ile Tyr Gly Gln Ala Val Glu Tyr Ser Gly Leu Val Arg
                2180                    2185                    2190

Val Gly Glu Asp Val Tyr Tyr Phe Gly Glu Thr Tyr Thr Ile Glu
                2195                    2200                    2205

Thr Gly Trp Ile Tyr Asp Met Glu Asn Glu Ser Asp Lys Tyr Tyr
                2210                    2215                    2220

Phe Asn Pro Glu Thr Lys Lys Ala Cys Lys Gly Ile Asn Leu Ile
                2225                    2230                    2235

Asp Asp Ile Lys Tyr Tyr Phe Asp Glu Lys Gly Ile Met Arg Thr
                2240                    2245                    2250

Gly Leu Ile Ser Phe Glu Asn Asn Asn Tyr Tyr Phe Asn Glu Asn
                2255                    2260                    2265

Gly Glu Met Gln Phe Gly Tyr Ile Asn Ile Glu Asp Lys Met Phe
                2270                    2275                    2280

Tyr Phe Gly Glu Asp Gly Val Met Gln Ile Gly Val Phe Asn Thr
                2285                    2290                    2295

Pro Asp Gly Phe Lys Tyr Phe Ala His Gln Asn Thr Leu Asp Glu
                2300                    2305                    2310

Asn Phe Glu Gly Glu Ser Ile Asn Tyr Thr Gly Trp Leu Asp Leu
                2315                    2320                    2325

Asp Glu Lys Arg Tyr Tyr Phe Thr Asp Glu Tyr Ile Ala Ala Thr
                2330                    2335                    2340

Gly Ser Val Ile Ile Asp Gly Glu Glu Tyr Tyr Phe Asp Pro Asp
                2345                    2350                    2355

Thr Ala Gln Leu Val Ile Ser Glu
                2360                    2365
```